US012280125B2

(12) United States Patent
Jermy et al.

(10) Patent No.: US 12,280,125 B2
(45) Date of Patent: Apr. 22, 2025

(54) METHOD FOR DELIVERING INSULIN

(71) Applicant: Imam Abdulrahman Bin Faisal University, Dammam (SA)

(72) Inventors: B. Rabindran Jermy, Dammam (SA); Vijaya Ravinayagam, Dammam (SA); Mohammed Salahuddin, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 130 days.

(21) Appl. No.: 17/941,384

(22) Filed: Sep. 9, 2022

(65) Prior Publication Data

US 2024/0082422 A1   Mar. 14, 2024

(51) Int. Cl.
*A61K 47/69* (2017.01)
*A61K 9/00* (2006.01)
*A61K 38/28* (2006.01)
*A61K 47/60* (2017.01)

(52) U.S. Cl.
CPC ........ *A61K 47/6923* (2017.08); *A61K 9/0053* (2013.01); *A61K 38/28* (2013.01); *A61K 47/60* (2017.08)

(58) Field of Classification Search
CPC .. A61K 47/6923; A61K 47/60; A61K 9/0053; A61K 38/28
See application file for complete search history.

(56) References Cited

U.S. PATENT DOCUMENTS

| | | | |
|---|---|---|---|
| 8,859,004 B2 | 10/2014 | Zhang et al. | |
| 9,259,456 B2 | 2/2016 | Kidron | |
| 10,653,732 B2 | 5/2020 | Ham et al. | |
| 10,668,024 B2 | 6/2020 | Liong et al. | |
| 2007/0087957 A1 | 4/2007 | Kidron | |
| 2020/0038525 A1* | 2/2020 | Jermy | A61K 47/6923 |

FOREIGN PATENT DOCUMENTS

| | | |
|---|---|---|
| CN | 106237191 A | 12/2016 |
| CN | 108421049 A | 8/2018 |
| HK | 1149195 B | 1/2014 |
| HK | 1217443 A | 1/2017 |
| IL | 192596 A | 9/2009 |

OTHER PUBLICATIONS

Asayama et al. Byproduct-Free intact modification of insulin by Cholesterol End-modified (Poly(ethylene glyco) for in vivo protein delievery. (Bioconjugate Chem, 2018, 29, 67-73; published Dec. 11, 2017) (Year: 2011).*
Desch et al. Microporous and Mesoporous Materials vol. 187, pp. 29-39. (Year: 2014).*
Jermy et al. Microporous and Mesoporous Materials, vol. 121, pp. 103-113. (Year: 2009).*
Trinh, et al. ; A novel injectable pH—temperature sensitive hydrogel containing chitosan-insulin electrosprayed nanosphere composite for an insulin delivery system in type I diabetes treatment ; Biomaterials Science, 8 ; May 13, 2020 ; 14 Pages.
Andreani, et al. ; Preparation and characterization of PEG-coated silica nanoparticles for oral insulin delivery ; International Journal of Pharmaceutics 473 ; Jul. 30, 2014 ; 9 Pages.
Maiorino, et al. ; The development of new basal insulins: is there any clinical advantage with their use in type 2 diabetes? ; Expert Opinion on Biological Therapy, vol. 14, Issue 6 ; Mar. 27, 2014 ; Abstract Only ; 4 Pages.
Aguirre, et al. ; Current status of selected oral peptide technologies in advanced preclinical development and in clinical trials ; Adv Drug Deliv Rev. 106(PtB) ; Nov. 15, 2016 ; Abstract Only ; 1 Page.

* cited by examiner

*Primary Examiner* — Katherine Peebles
(74) *Attorney, Agent, or Firm* — Oblon, McClelland, Maier & Neustadt, L.L.P.

(57) ABSTRACT

A method of delivering insulin, including: orally administering to a subject a composition containing a ferrisilicate material, polyethylene glycol, and insulin. The insulin at least partially penetrates pores of the ferrisilicate material to form a ferrisilicate insulin composite and the polyethylene glycol, at least partially enfolds the ferrisilicate insulin composite to form the composition. The composition has an insulin release rate of 10-50% after 100-500 hours following oral administration.

17 Claims, 20 Drawing Sheets

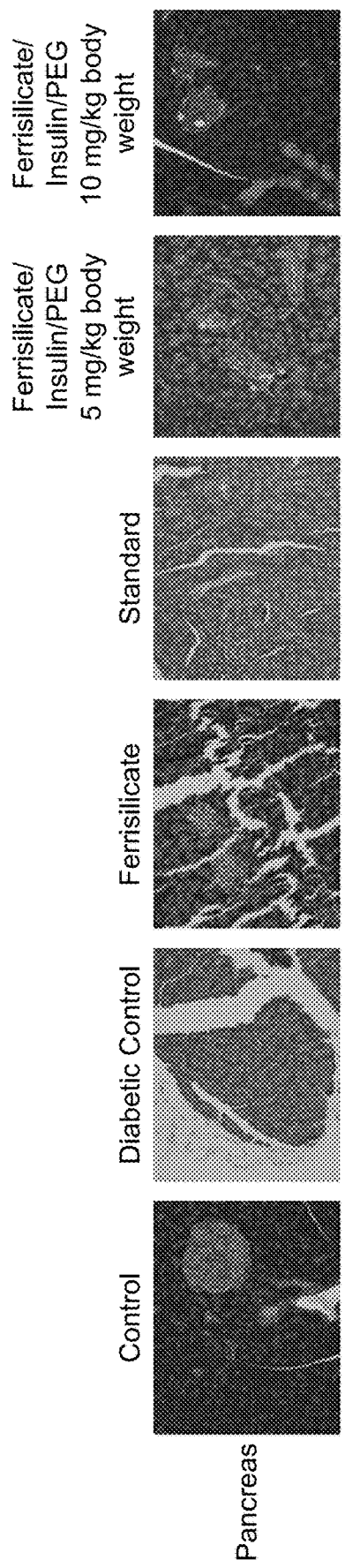
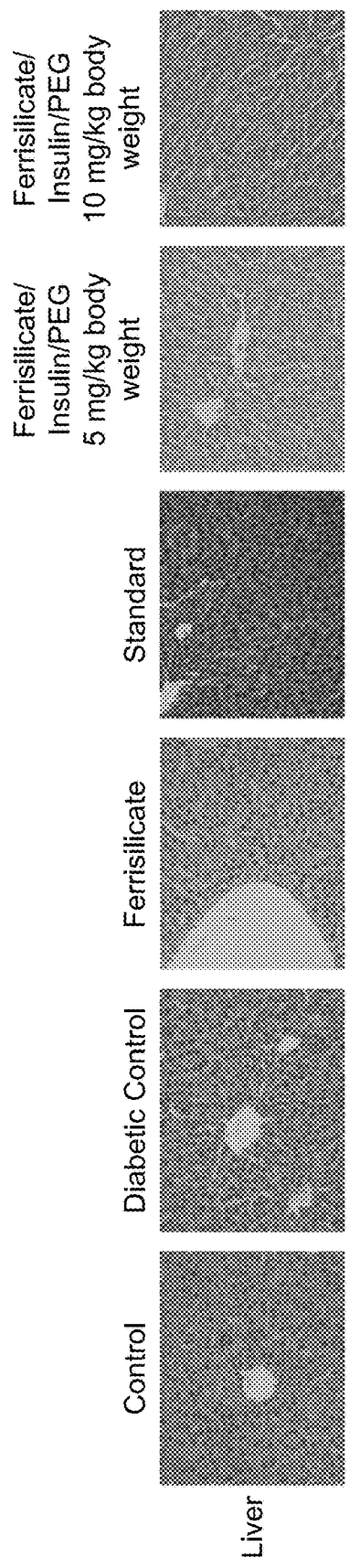

METHOD FOR DELIVERING INSULIN

BACKGROUND

Technical Field

The present disclosure is directed to a method for delivering insulin and particularly to a method for delivering insulin to a patient with diabetes mellitus.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Insulin is a peptide hormone produced by beta cells of the pancreas and is composed of 51 amino acids. It regulates the metabolism of carbohydrates, fats and protein by promoting the absorption of glucose from the blood into liver, fat and skeletal muscle cells. In these tissues the absorbed glucose is converted into either glycogen via glycogenesis or fats via lipogenesis.

Diabetes mellitus is a metabolic disorder categorized by hyperglycemia due to decreased or absent insulin secretion. Diabetic mellitus is differentiated as type I (no insulin is synthesized) and type II diabetes (insulin resistance). To treat diabetes, insulin is administered to patients to control their blood glucose levels. The conventional mode of administration of insulin to a patient is through injections. In order to treat diabetic mellitus type 1, about four injections per day may be required. Such treatment requires significant blood glucose monitoring by the patient and may induce several side effects such as lipoatrophy.

In order to limit the injection cycles, research has gone into a controlled insulin release strategy. One strategy included using zinc and protamine, but the formulation showed poor reproducible kinetic parameters, was not effective between meal periods and lead to hypoglycemic events (Holleman F, Gale E A. Nice insulins, pity about the evidence. Diabetologia. 2007 September; 50(9):1783-90). The construction of a stimuli responsive smart drug release system is the most recent research and employs a nanovehicle with controlled insulin delivery using biocompatible nanosilica. This is proposed to overcome the routine therapy deficiency, and improve the therapeutic efficiency, stability of drug release, ease of diet control and exercise regiments. Several glucose sensitive smart drug delivery systems based on phenylboronic acid (PBA), and proteins such as concanavalin and glucose oxidase have been reported (Najmeddine A A, Saeed M, Beadham I G, ElShaer A. Efficacy and safety of glucose sensors for delivery of insulin: A Systematic Review. PharmaNutrition. 2021 Dec. 1; 18:100280). One study prepared a glucose responsive system derived from PBA containing structured silica coated with diol based copolymers (N-acryloyl glucosamine and N-isopropyl acrylamide). The formulation showed a high loading capacity (14.7%) and encapsulation efficiency (85.9%) with glucose responsive release at pH=7.4 (Huang Q, Yu H, Wang L, Shen D, Chen X, Wang N. Synthesis and testing of polymer grafted mesoporous silica as glucose-responsive insulin release drug delivery systems. European Polymer Journal. 2021 Aug. 15; 157:110651). However, these properties still need to be improved before they can be administered to patients.

Drug delivery systems using biocompatible delivery sources such as structured silica/polymeric nanocomposites are known as promising nanovehicles to carry insulin (Kuang Y, Zhai J, Xiao Q, Zhao S, Li C. Polysaccharide/mesoporous silica nanoparticle-based drug delivery systems: A review. International Journal of Biological Macromolecules. 2021 Dec. 15; 193:457-73). Microneedle design based on mesoporous silica capped with zinc oxide in the form of an insulin reservoir has been reported to effectively control insulin delivery for a prolonged time duration (Fu Y, Liu P, Chen M, Jin T, Wu H, Hei M, Wang C, Xu Y, Qian X, Zhu W. On-demand transdermal insulin delivery system for type 1 diabetes therapy with no hypoglycemia risks. Journal of Colloid and Interface Science. 2022 Jan. 1; 605:582-91). The isomorphous substitution of biocompatible metals such as Fe, Zn, Ti etc., into the silica framework is gaining importance in biomedical applications (Tong X, Li Z, Chen W, Wang J, Li X, Mu J, Tang Y, Li L. Efficient catalytic ozonation of diclofenac by three-dimensional iron (Fe)-doped SBA-16 mesoporous structures. Journal of Colloid and Interface Science. 2020 Oct. 15; 578:461-70).

These methods suffer from one or more drawbacks, therefore, it is one object of the present disclosure to provide a method for delivering insulin to a patient. It is another object of the present disclosure to provide a method for sustained delivery of insulin to a patient. It is another object of the present disclosure to provide a method for delivery of insulin to a patient that is nontoxic. It is another object of the present disclosure to provide a method for delivery of insulin to a patient that can be administered orally. It is another object of the present disclosure to provide a method for delivery of insulin to a patient that has a high insulin loading capacity.

SUMMARY

In an exemplary embodiment, a method for delivering insulin is described. The method includes orally administering to a subject a composition including a ferrisilicate material, polyethylene glycol, and insulin. The insulin at least partially penetrates pores of the ferrisilicate material to form a ferrisilicate insulin composite. The polyethylene glycol at least partially enfolds the ferrisilicate insulin composite to form the composition. The composition has an insulin release rate of 10-50% after 100-500 hours following oral administration.

In some embodiments, the ferrisilicate material has an atomic ratio of silicon to iron of 10-300 to 1.

In some embodiments, the ferrisilicate material has cubic shaped pores.

In some embodiments, the insulin is amorphous.

In some embodiments, the composition has a surface area of 300-350 square meter per gram ($m^2/g$).

In some embodiments, the composition has a pore volume of 0.1-0.5 cubic centimeter per gram ($cm^3/g$).

In some embodiments, the composition has a pore size of 3-4 nanometers (nm).

In some embodiments, at least a portion of the polyethylene glycol is hydrogen-bonded to the insulin.

In some embodiments, the ferrisilicate insulin composite has 5-90 weight percent (wt. %) insulin based on a total weight of the ferrisilicate insulin composite.

In some embodiments, the ferrisilicate insulin composite has 60-80 wt. % insulin based on the total weight of the ferrisilicate insulin composite.

In some embodiments, the insulin is released from the composition in an environment with a pH of 5-9.

In some embodiments, the composition has no toxicity towards the subject up to a concentration of 300 microgram per milliliter (μg/mL).

In some embodiments, 1-100 milligrams (mg) of the composition per kg body weight of the subject is orally administered.

In some embodiments, a blood glucose level is decreased following oral administration.

In some embodiments, the blood glucose level is decreased by 5-40% after 1-3 hours following oral administration.

In some embodiments, the composition is administered daily.

In some embodiments, the blood glucose level is decreased by 20-50% after 28 days.

In some embodiments, the blood glucose level is decreased by a greater amount than a same method administering only the insulin.

In another exemplary embodiment, a composition for delivering insulin is described. The composition includes a ferrisilicate material, polyethylene glycol, and insulin. The insulin at least partially penetrates pores of the ferrisilicate material to form a ferrisilicate insulin composite. The polyethylene glycol at least partially enfolds the ferrisilicate insulin composite to form the composition.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIGS. 19A-F are images of pancreatic tissue after treatment with various formulations, according to certain embodiments of the present disclosure;

FIGS. 20A-F are images of liver tissue after treatment with various formulations, according to certain embodiments of the present disclosure.

DETAILED DESCRIPTION

Figure 1:
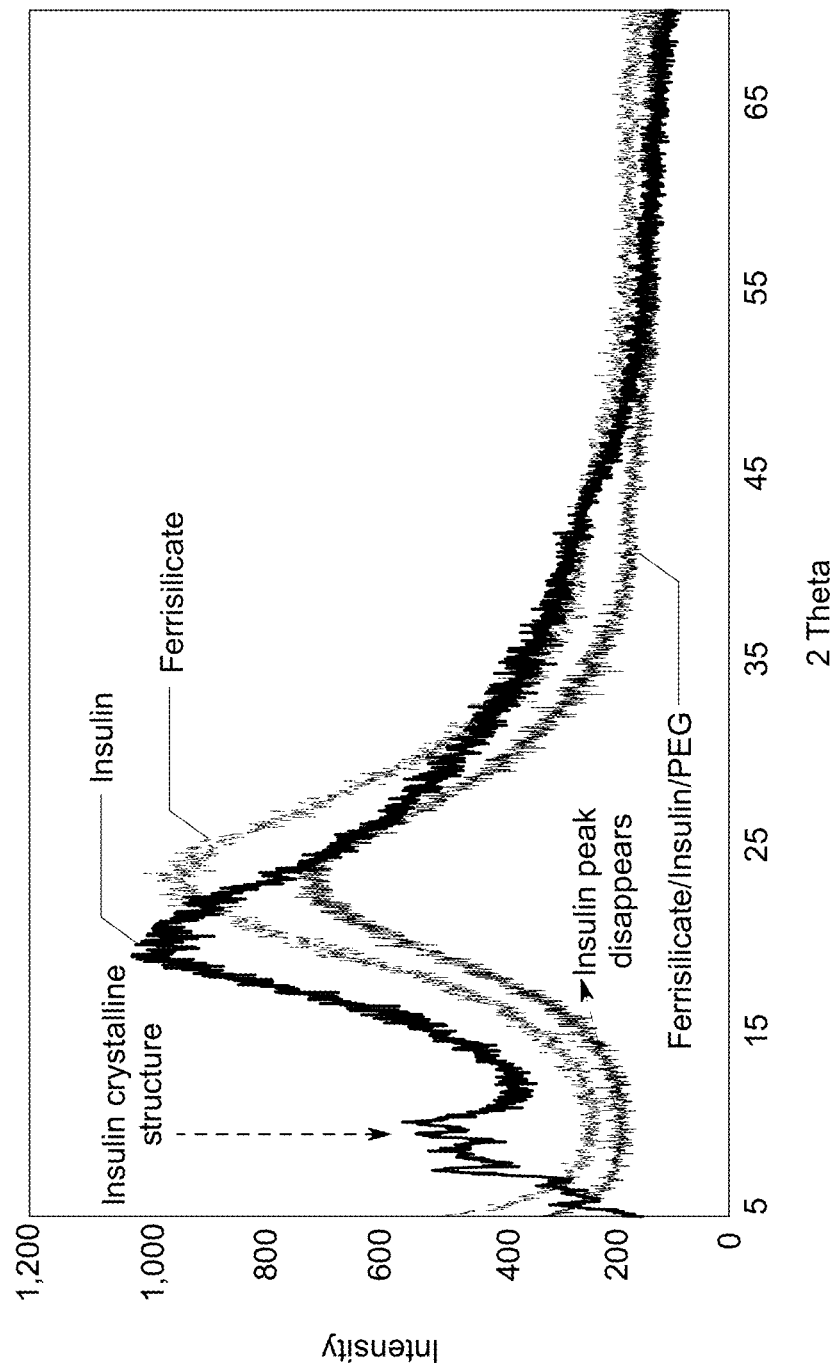
FIG. 1 is a graph depicting X-ray diffraction (XRD) patterns of insulin, ferrisilicate, and Ferrisilicate/Insulin/PEG, according to certain embodiments of the present disclosure.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

The term "zeolite" refers to microporous, aluminosilicate minerals commonly used as commercial adsorbents and catalysts. They are tetrahedral, three dimensional, crystalline minerals of aluminosilicate earth metals.

Aspects of the present disclosure are directed to a method of delivering insulin by orally administering a composition to a subject or patient. The composition is characterized by various analytical techniques, and the impact of the composition on blood glucose levels after administration is studied. The composition has low toxicity and diabetic management properties, thereby circumventing the drawbacks of the prior art.

In an embodiment, the composition includes a ferrisilicate material, polyethylene glycol, and insulin. A ferrisilicate material is defined throughout to the disclosure as a crystalline zeolite containing iron and silicon in the zeolite lattice positions. In an embodiment, the ferrisilicate material has an atomic ratio of silicon to iron of 10-300 to 1, preferably 10 to 1, 50 to 1, 100 to 1, 150 to 1, 200 to 1, 250 to 1, or 300 to 1. In an embodiment, the ferrisilicate material has cubic shaped pores. In some embodiments, the pores of the ferrisilicate material may include, but are not limited to, a cuboidal shape, a spherical shape, and a hexagonal shape. In an embodiment, the ferrisilicate material is iron modified from at least one silicate material, including but not limited to SBA-16, SBA-15, MSU-F, and/or ultra large pore FDU-12 (ULPFDU-12). In an embodiment, the ferrisilicate material is iron modified from the silicate material, SBA-16. In an embodiment, the ferrisilicate material has a Brunauer Emmett and Teller (BET) surface area of 700-900 $m^2/g$, preferably 750-850 $m^2/g$, or approximately 800 $m^2/g$. In an embodiment, the ferrisilicate material has a pore volume of 0.5-0.8 $cm^3/g$, preferably 0.6-0.7 $cm^3/g$, or approximately 0.65 $cm^3/g$. In an embodiment, the ferrisilicate material has a pore size of 2-5 nm, preferably 2.5-4.5 nm, 3-4 nm, or approximately 3.5 nm. In an embodiment, the ferrisilicate material has a particle size of 1-500 μm, preferably 50-450 μm, 100-400 μm, 150-400 μm, 200-350 μm, or 250-300 μm. In an embodiment, the ferrisilicate material has a Im3m, Ia3d, or a Pn3m phase. In an embodiment, the ferrisilicate material has a Im3m phase. In an embodiment, the ferrisilicate material has a surface area and pore size sufficient to accommodate macromolecules such as insulin.

In an embodiment, the insulin at least partially penetrates the pores of the ferrisilicate material to form a ferrisilicate insulin composite. In an embodiment, the insulin penetrates 10% of the pores in the ferrisilicate, preferably 20%, 30%, 40%, 50%, 60%, 70%, 80%, 90%, or 100%.

In an embodiment, the insulin is amorphous in the ferrisilicate insulin composite. In an embodiment, only the ferrisilicate exhibits an X-ray diffraction (XRD) peak at 10-40°, preferably 15-35°, 20-30°, or approximately 25°, in the ferrisilicate insulin composite. In some embodiments, the insulin may be crystalline in the ferrisilicate insulin composite. In an embodiment, the insulin exhibits an XRD peak at 5-12°, preferably 6-11°, 7-10°, or 8-9°. In one embodiment, the ferrisilicate insulin composite has 5-90 weight percent (wt. %) insulin based on a total weight of the ferrisilicate insulin composite, preferably 10-85 wt. %, 15-70 wt. %, 20-65 wt. %, 25-60 wt. %, 30-55 wt. %, 35-50 wt. %, or 40-45 wt. %. In an embodiment, ferrisilicate entraps at least 1%, preferably 2%, 3%, 4%, or 5%, more insulin than comparable silicate materials. In an embodiment, a comparable silicate material is a silicate material with substantially similar (±10%) pore size, volume, and shape to the ferrisilicate material but without iron present.

In an embodiment, polyethylene glycol (PEG) at least partially enfolds the ferrisilicate insulin composite. In some embodiments, the PEG enfolds 10% of the ferrisilicate insulin composite, preferably 20%, 30%, 40%, 50%, 60%, 70%, 80%, 90%, or 100%. In an embodiment, the PEG further includes ethylene glycol, or propylene glycol. In an embodiment, the PEG has a molecular weight of 100-8,000 g/mol, preferably 500-7,000 g/mol, 1,000-6,000 g/mol, 2,000-5,000 g/mol, or 3,000-4,000 g/mol. In an embodiment, the PEG has a molecular weight of approximately 400 g/mol±50 mg/mol, preferably ±30 mg/mol or ±10 mg/mol. In an embodiment, the PEG is used to make the ferrisilicate insulin composite biocompatible. In an embodiment, the PEG makes the composition hydrophilic. In an embodiment, at least a portion of the polyethylene glycol, preferably 20%, 30%, 40%, 50%, 60%, 70%, 80%, 90%, or 100%, is hydrogen-bonded to the insulin of the composition. In an embodiment, a hydroxyl (—OH) group on the PEG hydrogen bonds with an amine (—$NH_2$) on at least one of the amino acids of insulin. In some embodiments, the composition may also include surfactants, diluents (such as lactose, dextrose, sucrose, mannitol, sorbitol, cellulose, and glycine), and lubricants (such as silica, talc, stearic acid, and magnesium or calcium salts thereof), in addition to ferrisilicate, PEG, and insulin. In an embodiment, the composition is also labeled throughout as Ferrisilicate/Insulin/PEG.

In an embodiment, the Ferrisilicate/Insulin/PEG has a BET surface area of 300-400 $m^2/g$, preferably 325-375 $m^2/g$, or approximately 350 $m^2/g$. In an embodiment, the BET surface area of the Ferrisilicate/Insulin/PEG is smaller than that of the ferrisilicate indicating the presence of insulin in the ferrisilicate pores. In an embodiment, the Ferrisilicate/Insulin/PEG has a pore volume of 0.1-0.5 $cm^3/g$, preferably 0.2-0.4 $cm^3/g$, or approximately 0.3 $cm^3/g$. In an embodiment, the pore volume of the Ferrisilicate/Insulin/PEG is smaller than that of the ferrisilicate indicating the presence of insulin in the ferrisilicate pores. In an embodiment, the Ferrisilicate/Insulin/PEG has a pore size of 2-5 nm, preferably 2.5-4.5 nm, 3-4 nm, or approximately 3.5 nm.

A method of preparing the Ferrisilicate/Insulin/PEG composition according to certain embodiments is described. The order in which the method is described is not intended to be construed as a limitation, and any number of the described method steps can be combined in any order to implement the method. Additionally, individual steps may be removed or skipped from the method without departing from the spirit and scope of the present disclosure.

In an embodiment, the ferrisilicate is prepared by mixing a surfactant in acid for at least 1 hour, preferably 1-6 hours, 2-5 hours, or 3-4 hours to form a surfactant mixture. In an embodiment, the surfactant is poloxamer 407. In an embodiment, the acid is any strong acid known in the art, including but not limited to, hydrochloric acid, sulfuric acid, hydrobromic acid, or nitric acid. In an embodiment, the acid has a molarity (M) of 1-6, preferably 2-5, or 3-4. In an embodiment, the acid is 2M hydrochloric acid. In an embodiment, a silicate, a polar solvent, and an iron (III) salt are mixed into the surfactant mixture for at least 12 hours, preferably 12-48 hours, or 24-36 hours to form a reaction mixture. In an embodiment, the mass ratio of silicate to iron salt is 10-300 to 1, preferably 10 to 1, 50 to 1, 100 to 1, 150 to 1, 200 to 1, 250 to 1, or 300 to 1. In an embodiment, the silicate is tetraethylorthosilicate, tetramethylorthosilicate, tetrapropylorthosilicate, or tetrabutylorthosilicate. In an embodiment, the iron (III) salt is iron nitrate, iron sulfate, iron chloride, and hydrates thereof. In an embodiment, the polar solvent is water, ethanol, methanol, n-butanol, or t-butanol. In an embodiment, the reaction mixture was heated to at least 80° C., preferably 80-150° C., 90-140° C., 100-130° C., or 110-120° C. for at least 12 hours preferably 12-48 hours, or 24-36 hours to form a precipitate. In an embodiment, the precipitate is separated by filtration or decantation, and dried at a temperature of at least 80° C., preferably 80-150° C., 90-140° C., 100-130° C., or 110-120° C., for at least 12 hours, preferably 12-48 hours, or 24-36 hours to form uncalcined ferrisilicate. In an embodiment, the uncalcined ferrisilicate is calcined at a temperature of 400-700° C., preferably 500-600° C., or approximately 550° C., for at least 2 hours, preferably 2-10 hours, 3-9 hours, 4-8 hours, 5-7 hours, or approximately 6 hours to form the ferrisilicate.

In an embodiment, the ferrisilicate is loaded with insulin by mixing it in an acidic solution of insulin for a desired amount of time. In an embodiment, the acid is any strong acid known in the art, including but not limited to, hydrochloric acid, sulfuric acid, hydrobromic acid, or nitric acid. In an embodiment, the acid has a molarity of 0.01-1, preferably 0.02-0.08, or approximately 0.05. In an embodiment, the acid is 0.01 M hydrochloric acid. In an embodiment, the temperature of the acidic solution is 0-20° C., preferably 5-15° C., or approximately 10° C. In an embodiment, the mixing is for 0.1 to 12 hours, preferably 0.5-10 hours, 1-5 hours, or approximately 3 hours. In an embodiment, increased mixing times allows for higher adsorption of insulin into the ferrisilicate pores. In an embodiment, increased mixing times allows for higher adsorption of insulin into the ferrisilicate pores and results in slower release of insulin (discussed later in the description). In an embodiment, the insulin has a higher entrapment with longer mixing times. In an embodiment, the acidic solution is separated by filtration or decantation leaving a precipitate. The is dried at a temperature of 20-30° C., preferably 22-28° C., or approximately 25° C. for 2-10 hours, preferably 3-9 hours, 4-8 hours, or 5-6 hours to form the ferrisilicate insulin composite.

In an embodiment, the PEG is added to the ferrisilicate insulin composite by mixing the two materials at a temperature of 0-20° C., preferably 5-15° C., or approximately 10° C., for at least 12 hours, preferably 12-48 hours, or 24-36 hours to form the Ferrisilicate/Insulin/PEG.

In an aspect, the present disclosure provides a method of delivering insulin by administering to a subject the Ferrisilicate/Insulin/PEG composition. In an embodiment, the present disclosure provides a method of treating diabetes mellitus in a subject by administering to the subject the Ferrisilicate/Insulin/PEG composition. In an embodiment, diabetes mellitus is treated by reducing the blood glucose level in a subject with diabetes mellitus. In an embodiment, Ferrisilicate/Insulin/PEG releases insulin from the pores of the ferrisilicate into an environment. In an embodiment, the environment is inside the body of any animal. Animal refers to multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows. In an embodiment, the environment is a human body. In an embodiment, the environment is any mammal. In a preferred embodiment, the environment is a human with diabetes mellitus. In an embodiment, the environment is a saline or phosphate buffered solution.

In an embodiment, the method of treating diabetes mellitus includes orally administering the composition to the subject. In an example, the oral administration may include, but are limited to, tablets, pills, hard and soft capsules, liquids, suspensions, emulsions, syrups, powders, fine granules, granules, and pellets. In one embodiment, the tablets may include binders such as magnesium aluminum silicate, starch paste, gelatin, tragacanth, methyl cellulose, sodium carboxymethyl cellulose, and polyvinylpyrrolidone. In another embodiment, the tablets may include one or more pharmaceutical additives such as disintegrants including, but not limited to, starch, agar, alginic acid or a sodium salt thereof, absorbents, coloring agents, flavoring agents, and sweetening agents. In some embodiments, the composition may be administered parenterally, rectally, topically, transdermally, or subcutaneously.

In an embodiment, Ferrisilicate/Insulin/PEG releases at least 10% of the insulin, preferably 20%, 30%, 40%, 50%, 60%, 70%, or 80% following administration to the subject. In an embodiment, Ferrisilicate/Insulin/PEG releases insulin over 100-500 hours, preferably 150-450 hours, 200-400 hours, 250-350 hours, or approximately 300 hours. In an embodiment, Ferrisilicate/Insulin/PEG has an insulin release rate following oral administration of 10-50%, preferably 20-40% or approximately 30% after 100-500 hours, preferably 200-400 hours, or approximately 300 hours.

In an embodiment, Ferrisilicate/Insulin/PEG releases at least 5% more, preferably 10%, 15%, 20%, or 25% more insulin than comparable silicate materials after 500 hours. In an embodiment, Ferrisilicate/Insulin/PEG releases insulin in an environment with a pH of 1-9, preferably 2-7, 3-6, or 4-5. In an embodiment, Ferrisilicate/Insulin/PEG releases insulin in an environment with a pH of 5-9. In an embodiment, Ferrisilicate/Insulin/PEG releases at least 5% more, preferably 10%, 20%, 30%, 40%, or 50% more insulin in an environment with a pH of 6-8, compared to an environment with a pH of 1-3. In an embodiment, Ferrisilicate/Insulin/PEG prepared by mixing the ferrisilicate and insulin for 1 hour releases at least 5% less, preferably 10%, 15%, 20%, or 25% less insulin than Ferrisilicate/Insulin/PEG mixed for 0.1 hours, after 72 hours. In an embodiment, the insulin is more entrapped in the Ferrisilicate/Insulin/PEG prepared by mixing the ferrisilicate and insulin for 1 hour compared to 0.1 hours. In an embodiment, the cage shaped pores of the ferrosilicate allow for entrapment and sustained release of the insulin.

In an embodiment, the composition is non-toxic to the subject. In an embodiment, non-toxic means that no cell death is caused by the composition in the subject. In an embodiment, the composition has no toxicity towards human cells. In an embodiment, the composition has no toxicity towards human foreskin fibroblast (HFF-1) cells. In an embodiment, the composition has no toxicity towards HFF-1 cells up to a concentration of 300 microgram per milliliter (μg/mL), preferably 400 μg/mL, 500 μg/mL, 600 μg/mL, 700 μg/mL, 800 μg/mL, 900 μg/mL, or 1,000 μg/mL. In an embodiment, the composition decreases HFF-1 cell viability by less than 20%, preferably 15%, 10%, 5%, or 1%. In an embodiment, the composition decreases cell viability in a subject by less than 20%, preferably 15%, 10%, 5%, or 1%. The cell viability is the percentage of cells that survive following exposure to the composition.

In an implementation of the present disclosure, the composition may be orally administered based on a body weight of the patient. Particularly, a quantity of the composition is determined based on the body weight of the subject. In some embodiments, 1-100 milligrams (mg), preferably 10-90 mg, 20-80 mg, 30-70 mg, 40-60 mg, or approximately 50 mg of the composition per kg body weight of the subject is orally administered. Further, the quantity of the composition may be determined based on various factors such as diet of the subject, age of the subject, and medical condition of the subject in addition to the body weight.

In an embodiment, following oral administration, the blood glucose level of the subject decreases due to the release of insulin. Following oral administration, the blood glucose level of the subject decreases by 5-40%, preferably 10-35%, 15-30%, or 20-25% after 1-3 hours. In some embodiments, the composition may be administered daily. In an example, the daily administration of the composition may depend on various factors such as degree of progression of obesity, time of onset, age, diet, health condition, and complications of the subject to be administered. In some embodiments, the composition of the present disclosure may be generally administered once or several times a day. In an embodiment, the composition is administered when a subject exhibits a spike in blood glucose levels. In an embodiment, the composition can be administered to a subject for an extended period of time. In an embodiment, the composition can be used to maintain normal glucose levels in a subject. In an embodiment, with the administration of the composition, the blood glucose level of the subject is decreased by 20-50%, preferably 25-45%, 30-40%, or approximately 45% after 28 days, preferably 40 days, 50 days, or 100 days. In some embodiments, the blood glucose level is decreased by a greater amount than a same method administering only the insulin. The composition of the present disclosure can be used as a replacement for insulin injections in a subject with diabetes mellitus.

EXAMPLES

The following examples describe and demonstrate exemplary embodiments of the composition for delivering the insulin to the subject described herein. The examples are provided solely for the purpose of illustration and are not to be construed as limitations of the present disclosure, as many variations thereof are possible without departing from the spirit and scope of the present disclosure.

Example 1: Synthesis of Ferrisilicate Using Hydrothermal Technique

Tetraethylorthosilicate, silica source, pluronic F127, non-ionic template; iron nitrate, recombinant insulin, polyethylene glycol (molecular weight of 400) were obtained from Sigma Aldrich. Deionized water and n-butanol solvent were also used.

Iron incorporated structured SBA-16 (mesoporous silica) silica was prepared using a sol-gel technique. The Pluronic F127 was used as template, while the tetraethylorthosilicate (reagent grade, 98%) was used as the silica source. 5 grams (g) of the Pluronic F127 was dissolved in acidic HCl solution (2 molars (M)) and allowed to stir for 1 hour. Further 16 g of n-butanol (co-solvent) was added along with 24 g of the tetraethylorthosilicate and iron nitrate nonahydrate (Si/Fe ratio ranging between 40-250 (for 250 Si/Fe and 40 Si/Fe ratios require 0.186 g and 1.16 g of the iron nitrate nonahydrate)) and stirred for 24 hours to form a mixture. The mixture in a polypropylene bottle was transferred to an oven and hydrothermally aged at 100 degrees Celsius (° C.) for 24 hours. A precipitate was filtered, washed several times with excess water and dried at 100° C. for 12 hours. The synthesized sample was calcined at 550° C. for 6 hours.

Example 2: Synthesis of Iron Impregnated Structured KIT-6 or Mesosilicate Silica Using Impregnation Technique 0.7235 g of the iron nitrate nonahydrate was added in 80 ml of water and was stirred until dissolved. Further, 1.0 g (1000 mg) of KIT-6 or mesosilicalite was added and stirred for 24 hours at room temperature (RT). Then a material was dried at 120° C. for 3 hours and recovered and calcined at 500° C. for 2 hours. The samples are labeled throughout as Fe/KIT-6 and Fe/Mesosilicate.

Example 3: Synthesis of Ferrisilicate/Insulin

For the insulin loading, 80 mg of the insulin was taken in 8 ml of 0.01 M HCl solution and stirred for 20 minutes. Then 160 mg of the ferrisilicate was added and stirred at 300 rotations per minute (rpm) overnight in an ice cool environment. After that a solution mixture was filtered, washed with 5 ml $H_2O$ and dried at RT (5 hours) and stored at 4° C. The Fe/KIT-6 and Fe/Mesosilicate samples were also loaded with insulin and labeled throughout as Fe/KIT-6/Insulin and Fe/Mesosilicate/Insulin.

Example 4: Synthesis of Ferrisilicate/Insulin/PEG

For PEGylation, 14 microliters ($\mu L$) of the PEG (molecular weight of 400) was added in 3 ml of deionized water, stirred for 20 minutes under argon atmosphere, then 150 mg of the Ferrisilicate/Insulin was added and stirred under the ice cool environment for 24 hours. Then a solution mixture was freeze dried using a lyophilization technique. The Fe/KIT-6/Insulin and Fe/Mesosilicate/Insulin.samples were also pegylated and labeled throughout as Fe/KIT-6/Insulin/PEG and Fe/Mesosilicate/Insulin/PEG. This also applied to mesocellular foam MSU-F labeled as Mesocellular foam/Insulin/PEG.

Example 5: Characterization Techniques

The phase of the insulin, and Ferrisilicate/Insulin/PEG was identified using X-Ray diffraction (XRD) (Miniflex 600, Rigaku, Japan). Textural features including Brunauer-Emmett-Teller (BET) surface area, pore size and pore volume were measured using nitrogen adsorption technique (ASAP-2020 plus, Micromeritics, USA). Ferrite nanoparticle chemical coordination was analyzed using differential reflectance spectroscopy-ultraviolet-visible (DRS-UV-vis spectroscopy analysis (JASCO, Japan)). Insulin functional groups of the composition were determined using Fourier transform infrared spectroscopy (FT-IR) spectroscopy (Perkin Elmer). Morphological variations of the Ferrisilicate/Insulin/PEG were investigated using transmission electron microscopy (TEM, JEM2100F, JEOL).

Example 6: Insulin Release Study

A release trend among various formulations were studied using a dialysis membrane technique. 30 mg of the formulation was placed inside 3 ml of phosphate-buffered saline (PBS) solution inside the dialysis membrane. The release of the insulin was monitored under different pH solutions (7.4, 6.8 and 1.2) at 37° C. At regular time interval, 10 ml of the PBS solution was withdrawn and replaced with equal volume of a fresh solution. The release amount of the insulin was identified at specific wavelength of 275 nm.

Example 7: In-Vitro Study of Ferrisilicate/Insulin/PEG on HFF-1 Cells

Figure 11:
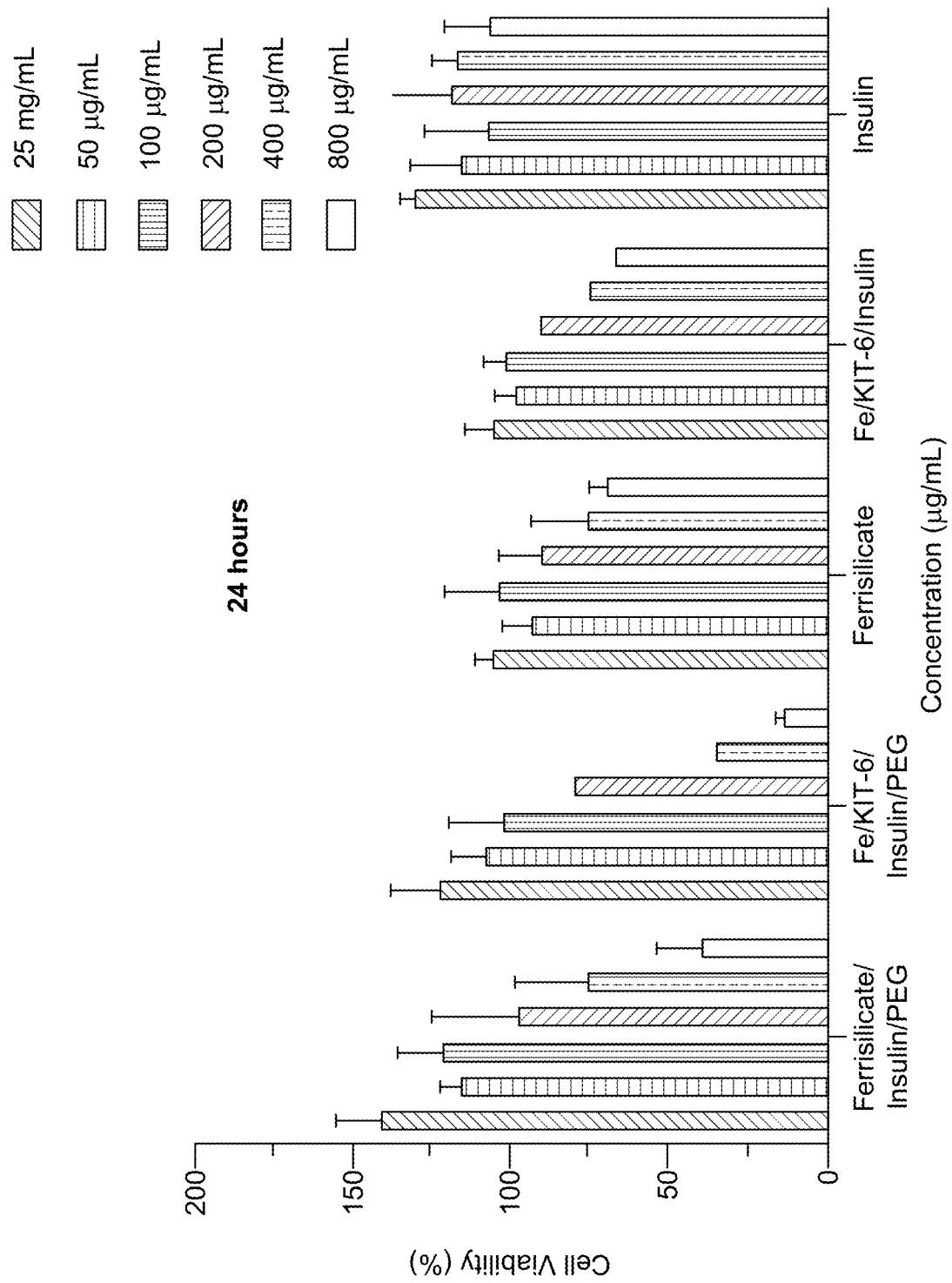
FIG. 11 is a bar graph depicting cell viability of human foreskin fibroblast (HFF-1) cells, treated with various formulations for 24 hours, according to certain embodiments of the present disclosure.
Figure 12:
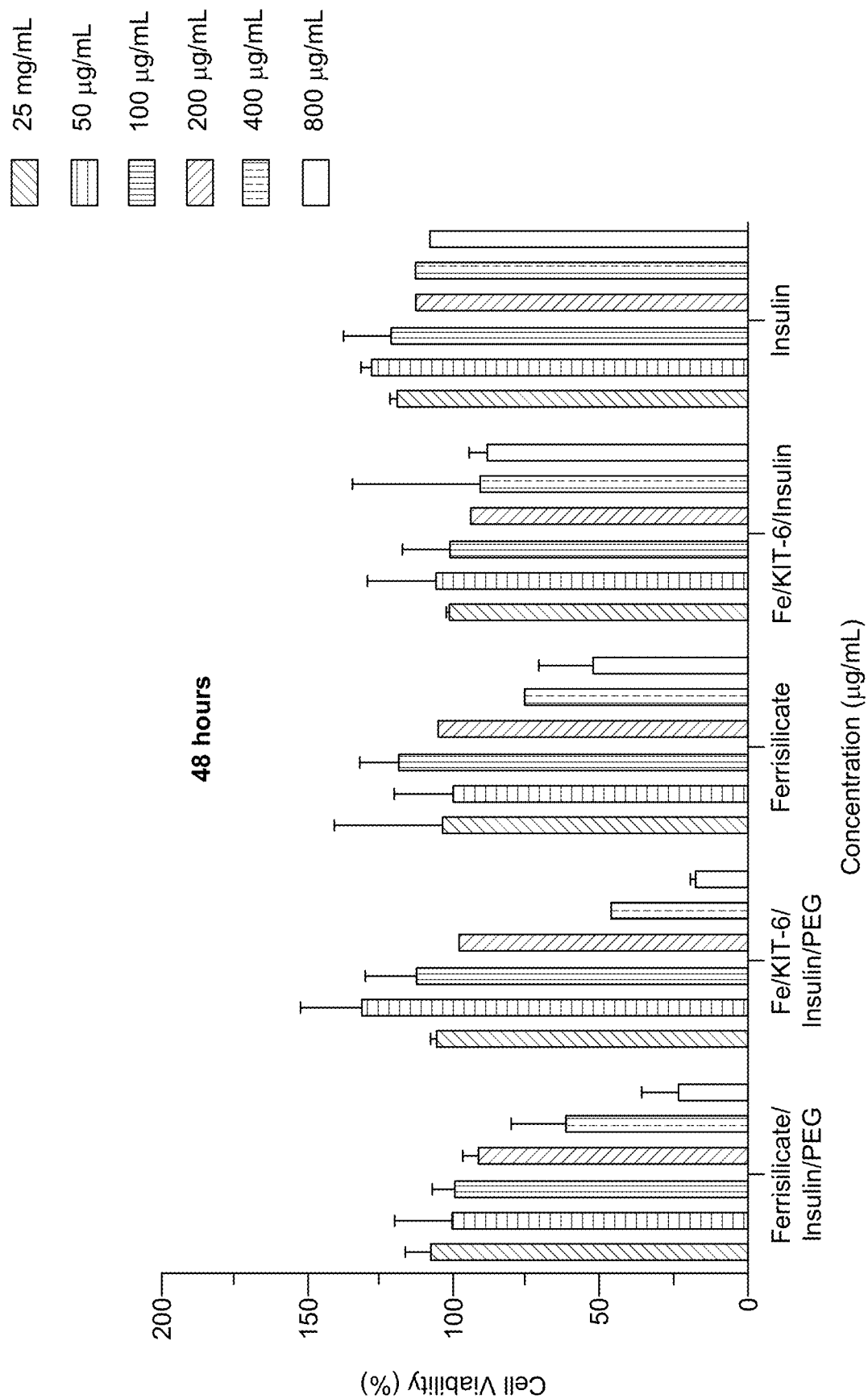
FIG. 12 is a bar graph depicting cell viability study of HFF-1 cells, treated with various formulations for 48 hours, according to certain embodiments of the present disclosure.
Figure 13:
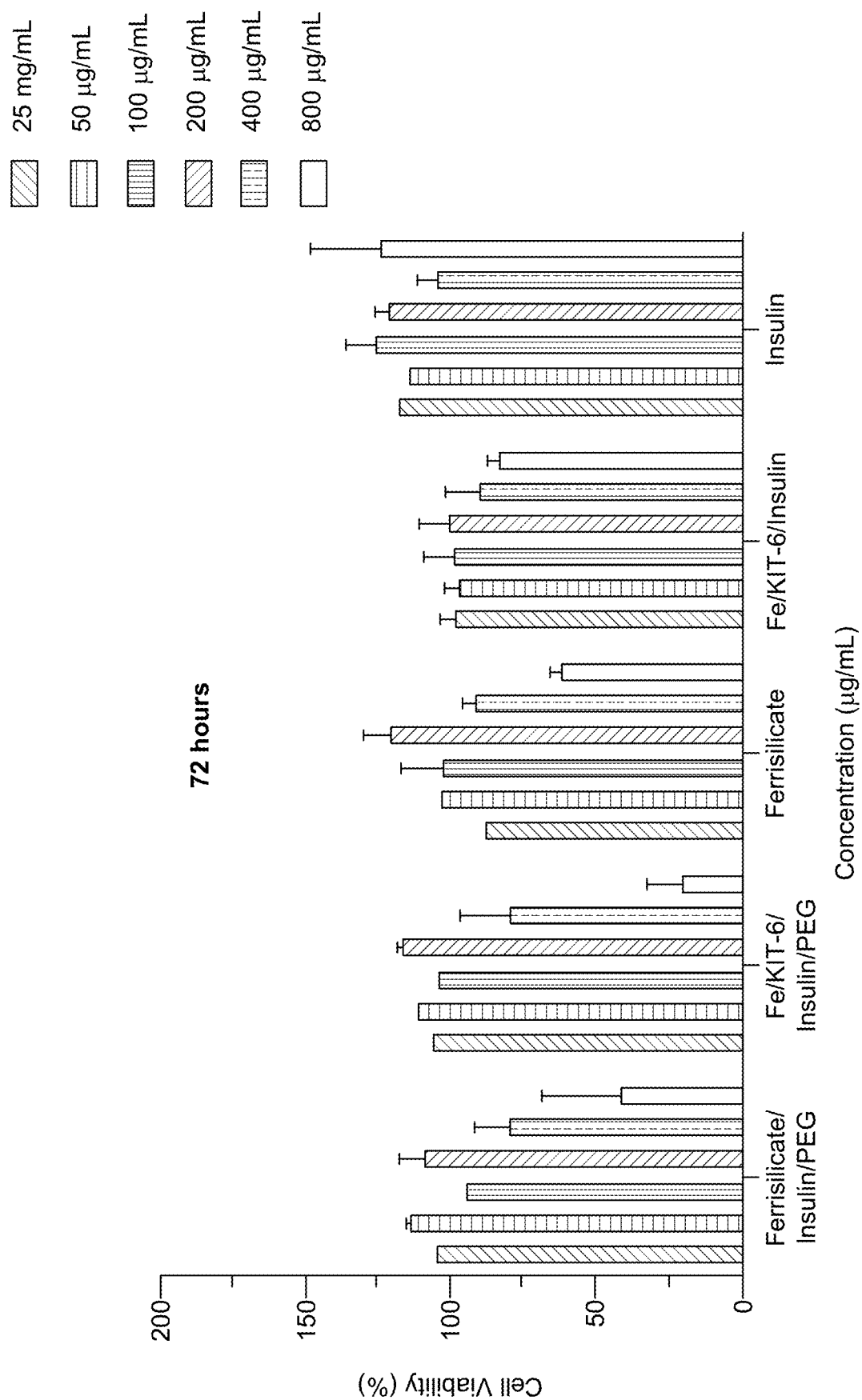
FIG. 13 is a bar graph depicting cell viability study of HFF-1 cells, treated with various formulations for 72 hours, according to certain embodiments of the present disclosure.

Human foreskin fibroblast (HFF-1) cells were obtained as (ATCC© SCRC-1041TM) and maintained in Dulbecco's modified eagle medium (DMEM) supplied with 10% fetal bovine serum, 1% L-glutamine and 1% penicillin-streptomycin (Gibco, Thermo Fisher Scientific, Massachusetts, United States) in 5% $CO_2$ under humidity at 37° C. The cells were seeded in 96-well plate at (104 cells/well) and treated with Ferrisilicate/Insulin/PEG, Fe/KIT-6/Insulin/PEG, ferrisilicate, Fe/KIT-6/Insulin using 25, 50, 100, 200, 400, 800 μg/mL and the insulin at 12.5, 25, 50, 100, 200 and 400 μg/mL for 24, 48 and 72 hours (cell viability studies are shown in FIGS. 11-13, respectively). 3-(4,5-dimethylthiazol-2-yl)-2,5-diphenyltetrazolium bromide (MTT) was carried out after washing well plates with 1×PBS and changing media. MTT reagent (Sigma-Aldrich M2128-1G, UK) was added to the media to have a final dilution at 1:10 and incubated in 5% $CO_2$ under humidity at 37° C. for 4 hours. Formed Formazan dye was solubilized by adding 100 μl of dimethyl sulfoxide (DMSO) and read at 570 nm wavelength by SYNERGY Neo2 multi-mode microplate reader (BioTek Instruments Vermont, United States). Cell viability was calculated by using equation (1).

$$\text{Cell viability (\%)} = \text{AbsSample/AbsControl } 100 \quad (1)$$

The cell viability assay was performed in five independent experiments (n=5). Statistical analysis was performed using Prism 9 software (GraphPad, La Jolla, CA). The analysis was performed using one-way ANOVA with Dunnett's post hoc test. Error bars±S.E.M. * $p<0.05$;  $p<0.01$; * $p<0.001$; **** $p<0.0001$ versus control. In case there was no indication of significance, which indicates that results were non-significant. Data analysis of drug delivery was done using Prism 8 software and SPSS software version 20.0.

Example 8: Formulation Morphology

FIG. 1 depicts an XRD pattern of insulin, ferrisilicate, Ferrisilicate/Insulin/PEG. The recombinant insulin powder exhibited crystalline peaks (2 theta range 5-15°) characteristics of the macrostructured protein. The ferrisilicate exhibited a broad amorphous silica peak between 10-40°. In the Ferrisilicate/Insulin/PEG, a crystalline peak of the insulin was absent, which indicated the molecular dispersion or amorphous transformation on the ferrisilicate.

Figure 2:
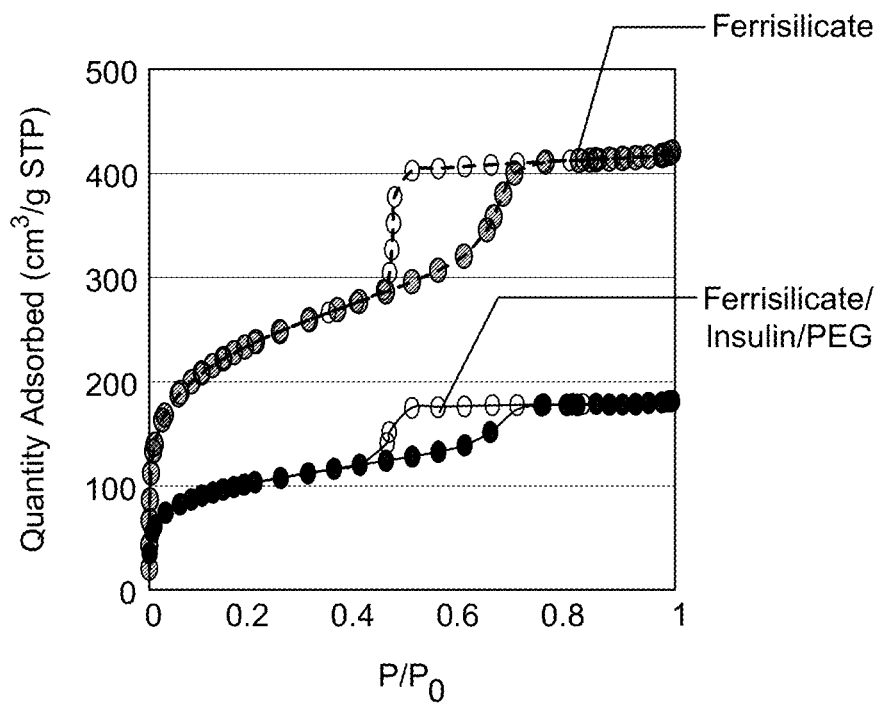
FIG. 2 is a graph depicting nitrogen adsorption isotherm of ferrisilicate, and Ferrisilicate/Insulin/PEG, according to certain embodiments of present disclosure.
Figure 3:
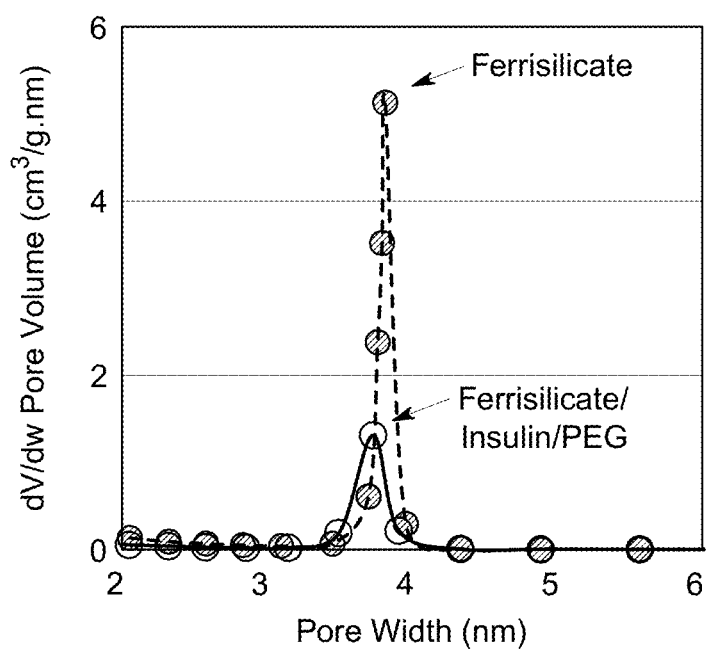
FIG. 3 is a graph depicting pore size distributions of ferrisilicate, and Ferrisilicate/Insulin/PEG, according to certain embodiments of the present disclosure.
Figure 4:
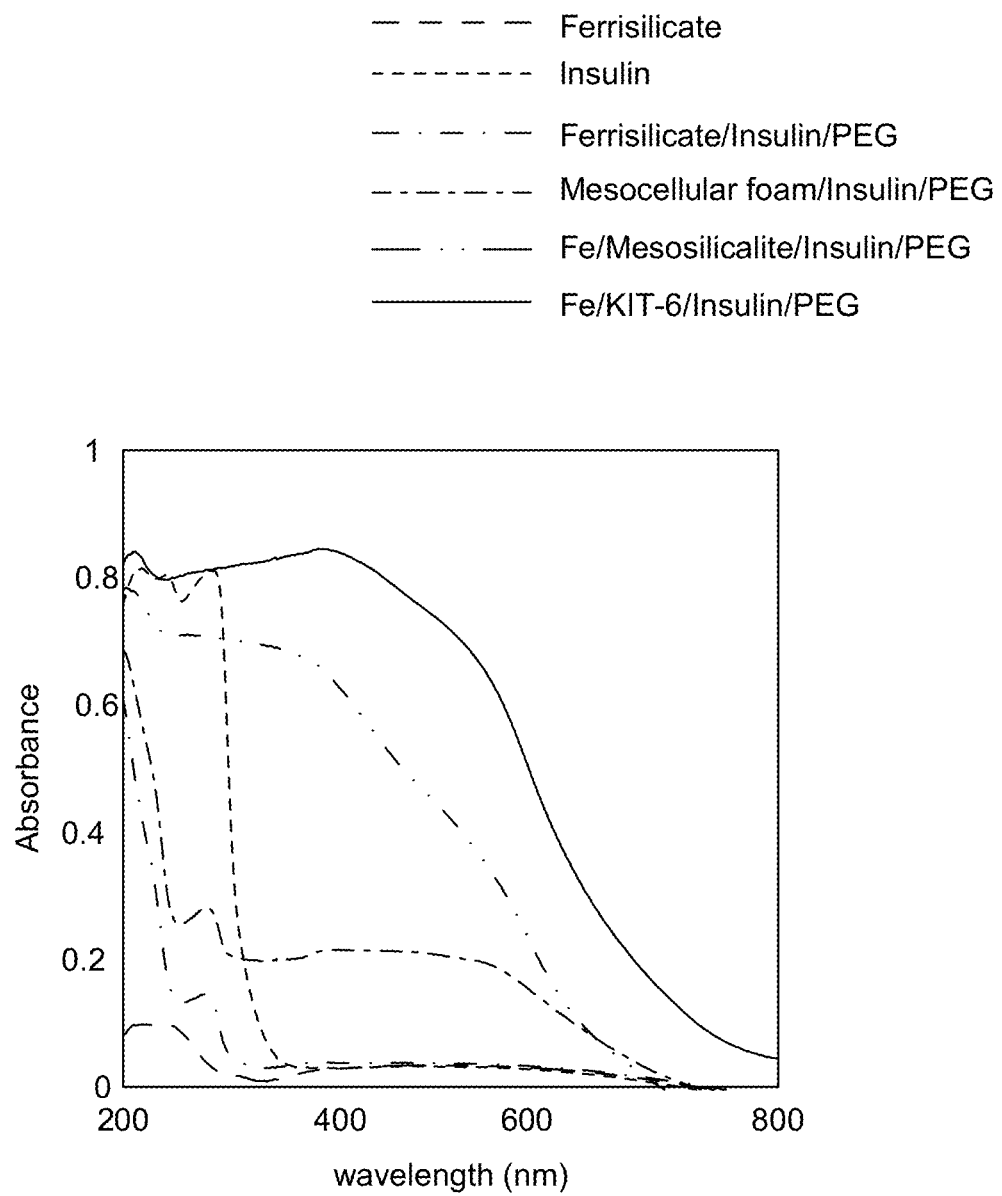
FIG. 4 is a graph depicting diffuse reflectance of ferrisilicate, Ferrisilicate/Insulin/PEG, insulin, Mesocellular foam/Insulin/PEG, Fe/Mesosilicalite/Insulin/PEG, and Fe/KIT-6/Insulin/PEG, according to certain embodiments of the present disclosure.

Nitrogen adsorption isotherm was used to characterize the surface texture and pore diameter of mesoporous materials in a range between 2-50 nm. The ferrisilicate surface texture along with three-dimensional (3D) cubic pore changes before and after the insulin and PEG modifications were analyzed (FIG. 2 and FIG. 3). Parent ferrisilicate with Im3m space group in the calcined form exhibited a type IV isotherm pattern with surface area of 804 m²/g, pore volume of 0.64 cm³/g and pore size centered at about 3.2 nm. After insulin loading and the PEG wrapping, the quantity of the nitrogen adsorbed reflected on peak height decreases with steepness in capillary condensation. Hysteresis loop slightly reduces indicating the pore occupation of the insulin. In parallel, the surface area (334 m²/g) and pore volume (0.27 cm³/g) reduce, while pore size remains at about 3.3 nm. Overall, the textural modification indicates the insulin deposition in cubic cage pores of the ferrisilicate (FIG. 2 and FIG. 3). DRS-UV-vis spectra of the ferrisilicate, the Ferrisilicate/Insulin/PEG, the insulin, the Mesocellular foam/Insulin/PEG, the Fe/Mesosilicalite/Insulin/PEG, and the Fe/KIT-6/Insulin/PEG are shown in FIG. 4. The ferrisilicate had a broad adsorption band in 200-300 nm with peak maxima at 216 and 245 nm. The presence of high energy band was ascribed to ligand to metal charge transfer due to tetrahedral $Fe^{3+}$ species. The band at 216 nm and 245 nm was ascribed to the electronic transition of $O^{2-}$ to $t_{2g}$ and $e_g$ orbitals of $Fe^{3+}$ in iron oxide cluster.

Unlike iron oxide loaded mesoporous silica, the ferrisilicate showed a broad unresolved absorption band expanding between 400 and 500 nm. The absorption at 400 and 500 nm were ascribed to the quantum size effect of alpha-$Fe_2O_3$ species. The ferrisilicate had $Fe^{3+}$ species and few hexacoordinated alpha-$Fe_2O_3$ (as shown in FIG. 4). Such species occurs with octahedral or distorted octahedral coordination. Formation of iron oxide species aggregated formed inside the cubic pore channels of the ferrisilicate. The insulin binding ability of the ferrisilicate was measured using DRS-UV-Visible spectra. The insulin showed a strong absorption band at about 285 nm. The ferrisilicate loaded with the insulin (50 wt/wt %) loading followed by washing showed a similar peak to that of the insulin at about 281 nm. The PEG wrapping resulted in effective conjugation with insulin through hydrogen bonding (as shown in FIG. 4). The PEG hydroxyl group interaction with amine functional moiety of amino acids of the insulin is known.

Figure 5:
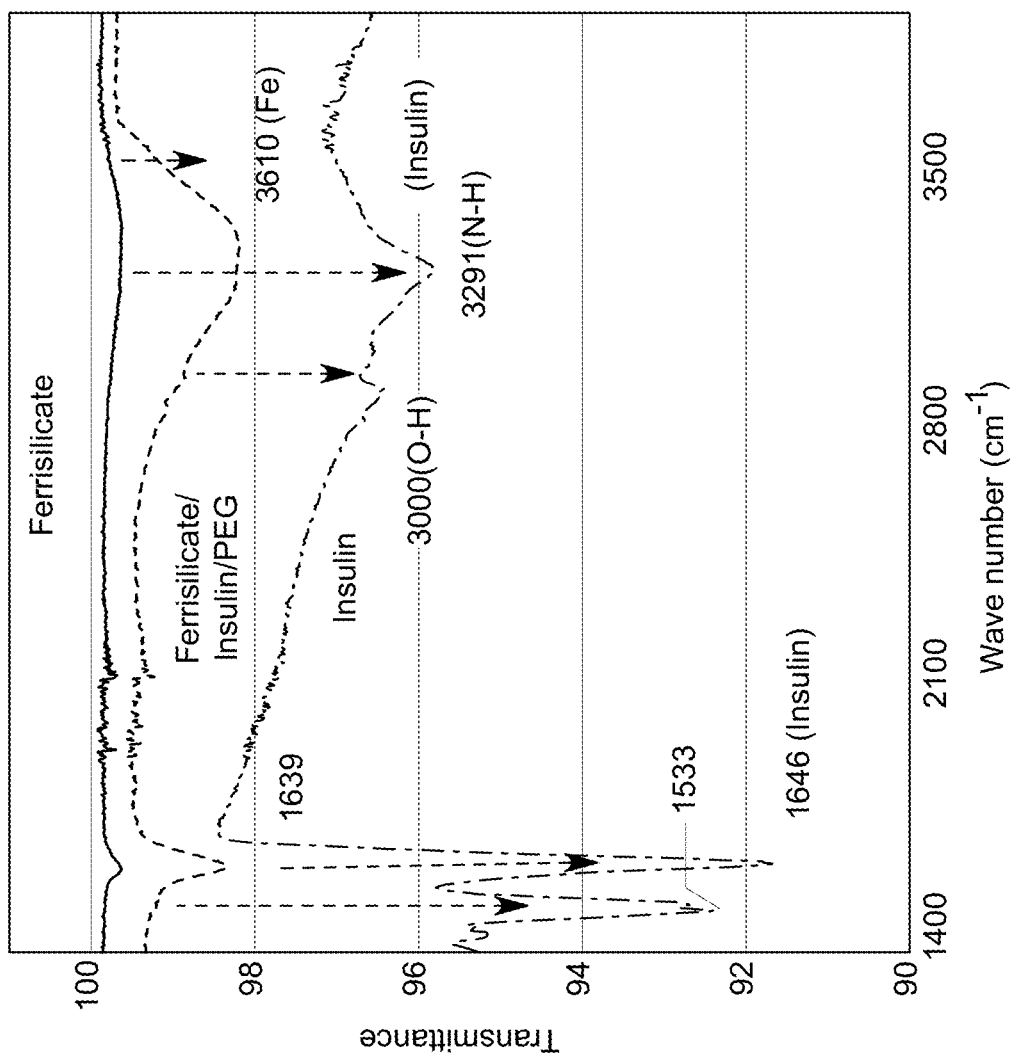
FIG. 5 is a graph depicting Fourier transform infrared spectroscopy (FT-IR) spectra of ferrisilicate, Ferrisilicate/Insulin/PEG, and insulin, according to certain embodiments of the present disclosure.

FT-IR spectrum of the ferrisilicate, the Ferrisilicate/Insulin/PEG and the insulin is shown in FIG. 5. The ferrisilicate exhibited characteristics peaks at hydroxyl region between 3730 cm$^{-1}$ to 3610 cm$^{-1}$. The presence of broad band at about 3610 cm$^{-1}$ was attributed to the hydroxyl group bridging signaling Bronsted sites related to isomorphous substitution of Fe for Si in the framework of ferrisilicate. The insulin showed the characteristics carbonyl (C=O) stretching vibration bands due to amide at 1646 cm$^{-1}$ and 1533 cm$^{-1}$, respectively.

In case of the Ferrisilicate/Insulin/PEG, characteristics insulin vibration bands appear at about 1639 cm$^{-1}$ and 1518 cm$^{-1}$. An increase in such vibration peaks showed the insulin coupling with the ferrisilicate. Moreover, there was a shift in the insulin main vibration bands of insulin occurs from 1646 cm$^{-1}$ to 1639 cm$^{-1}$. Such shifting of bands after functionalization of insulin indicated the effective interaction between insulin and ferrisilicate. The insulin loading capacity and entrapment inside the pore channels played a role in release and anti-diabetic activity. An elongation in the broad hydroxyl (3000 cm$^{-1}$) and amine stretching (3291 cm$^{-1}$) compared to the ferrisilicate indicated the effective functionalization of the insulin in the Ferrisilicate/Insulin/PEG composition.

Figure 21B:
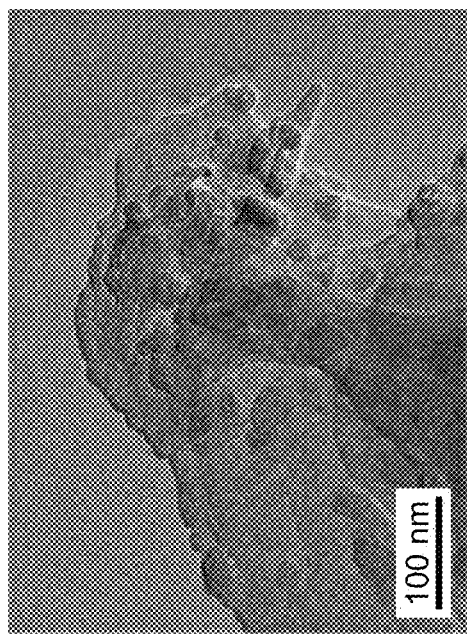
FIGS. 21A-D are transmission electron microscope (TEM) images of ferrisilicate and Ferrisilicate/Insulin/PEG, according to certain embodiments of the present disclosure.
Figure 21D:
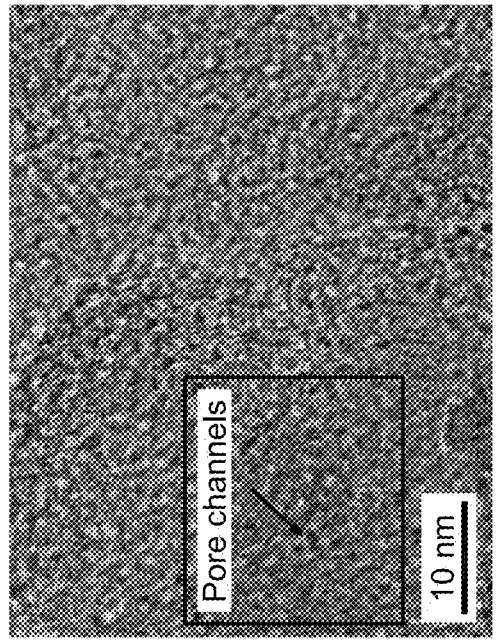
Figure 21A:
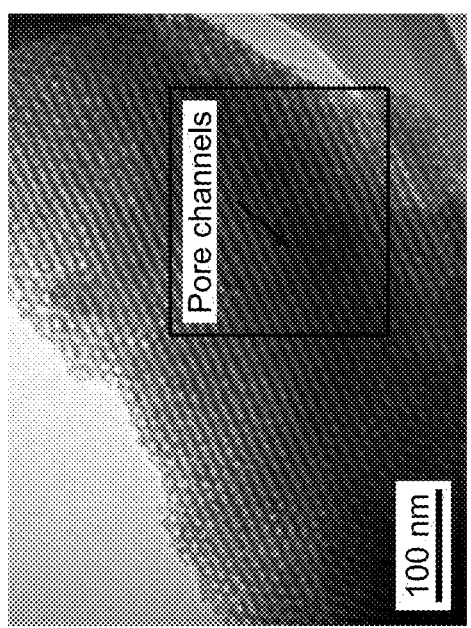
Figure 21C:
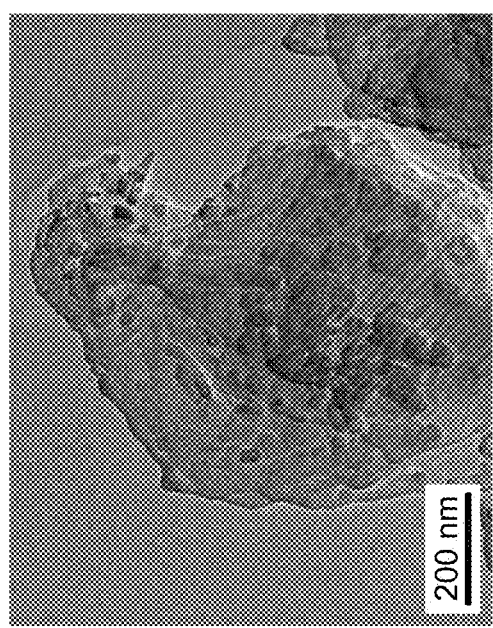

Transmission electron microscope (TEM) images of ferrisilicate alone are shown in FIGS. 21A-B and TEM images of Ferrisilicate/Insulin/PEG are shown in FIGS. 21C-D. The ferrisilicate has uniform pore channels running in the parallel directions, whereas there is a change in morphology of the Ferrisilicate/Insulin/PEG due to the pores filling with insulin and PEG wrapping. Again, indicating the effective functionalization of the insulin in the Ferrisilicate/Insulin/PEG composition.

Example 9: Insulin Adsorption and Release of the Formulations

Figure 6:
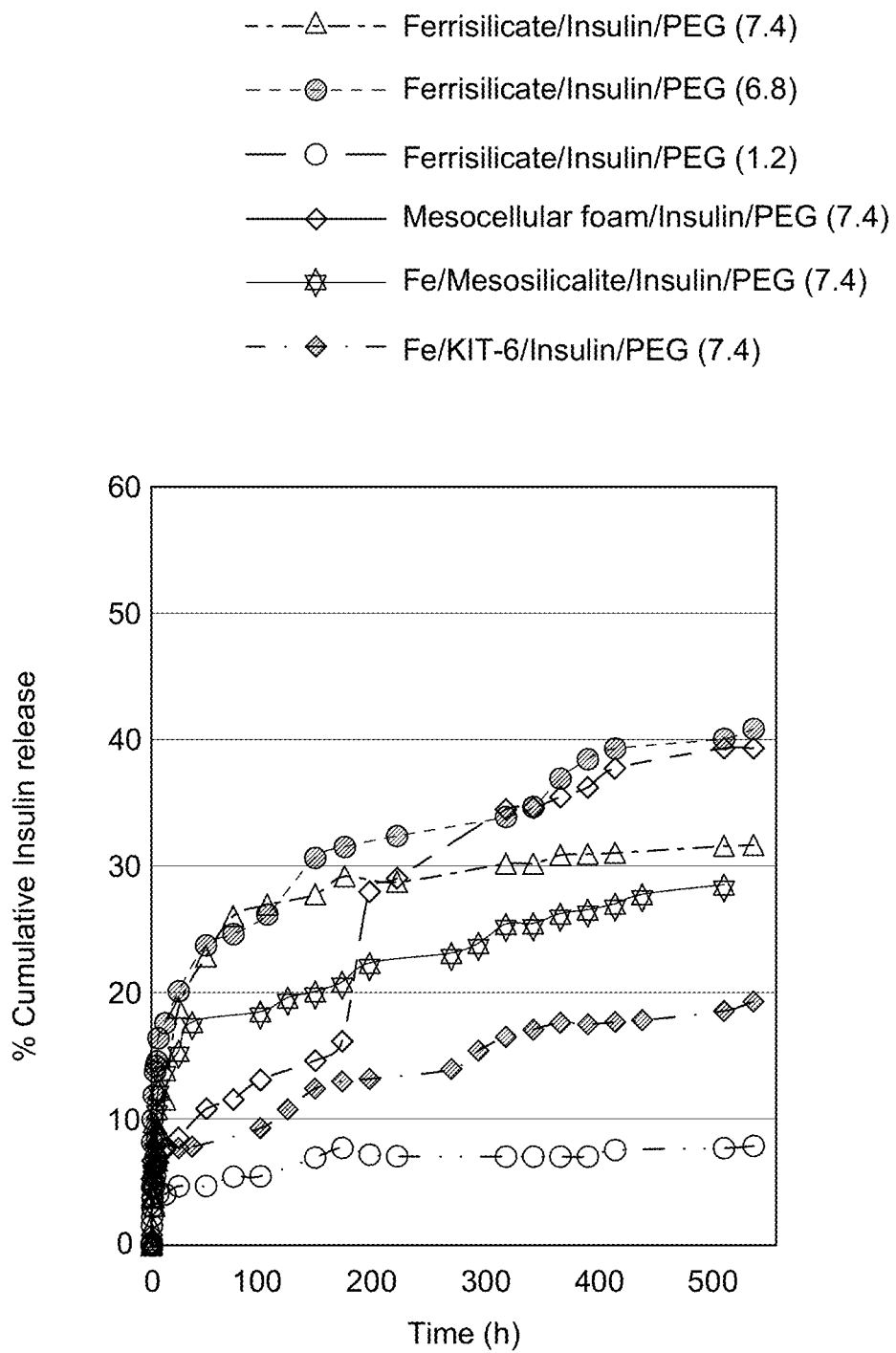
FIG. 6 is a graph depicting cumulative insulin release of Ferrisilicate/Insulin/PEG at a pH of 1.2, 6.8, and 7.4, and Mesocellular foam/Insulin/PEG, Fe/Mesosilicalite/Insulin/PEG, and Fe/KIT-6/Insulin/PEG at a pH of 7.4, at various pH conditions, according to certain embodiments of the present disclosure.

The insulin release of Ferrisilicate/Insulin/PEG, Mesocellular foam/Insulin/PEG, Fe/Mesosilicalite/Insulin/PEG, and Fe/KIT-6/Insulin/PEG at different pH conditions (7.4, 6.8 and 1.2) for 72 hours is shown in FIG. 6. Percentage cumulative release profile of the insulin over the Ferrisilicate/Insulin/PEG was found to be high at about 40-50% followed by Fe/Mesosilicalite/Insulin/PEG and Fe/KIT-6/Insulin/PEG, which contains a three-dimensional pore architecture showed a release of about 25% for 72 hours. The present observation indicates ink shaped pores of SBA-16 (about 3.3 nm) are slightly restricted with Fe impregnation (ferrisilicate) and showed a sustained release behavior with respect to other silicate materials. The presence of 3D cage type pores with Ia3d structure of KIT-6 was found to favor the slow release of the insulin (18% for 490 hours), while the mesosilicalite with hexagonal pores of mesosilicalite showed a release of about 27% for 490 hours. The present observation indicates that the insulin tended to functionalize on the external micropores of the mesosilicalite, while the cage type pores were able to accommodate the insulin inside the mesopores.

Figure 7:
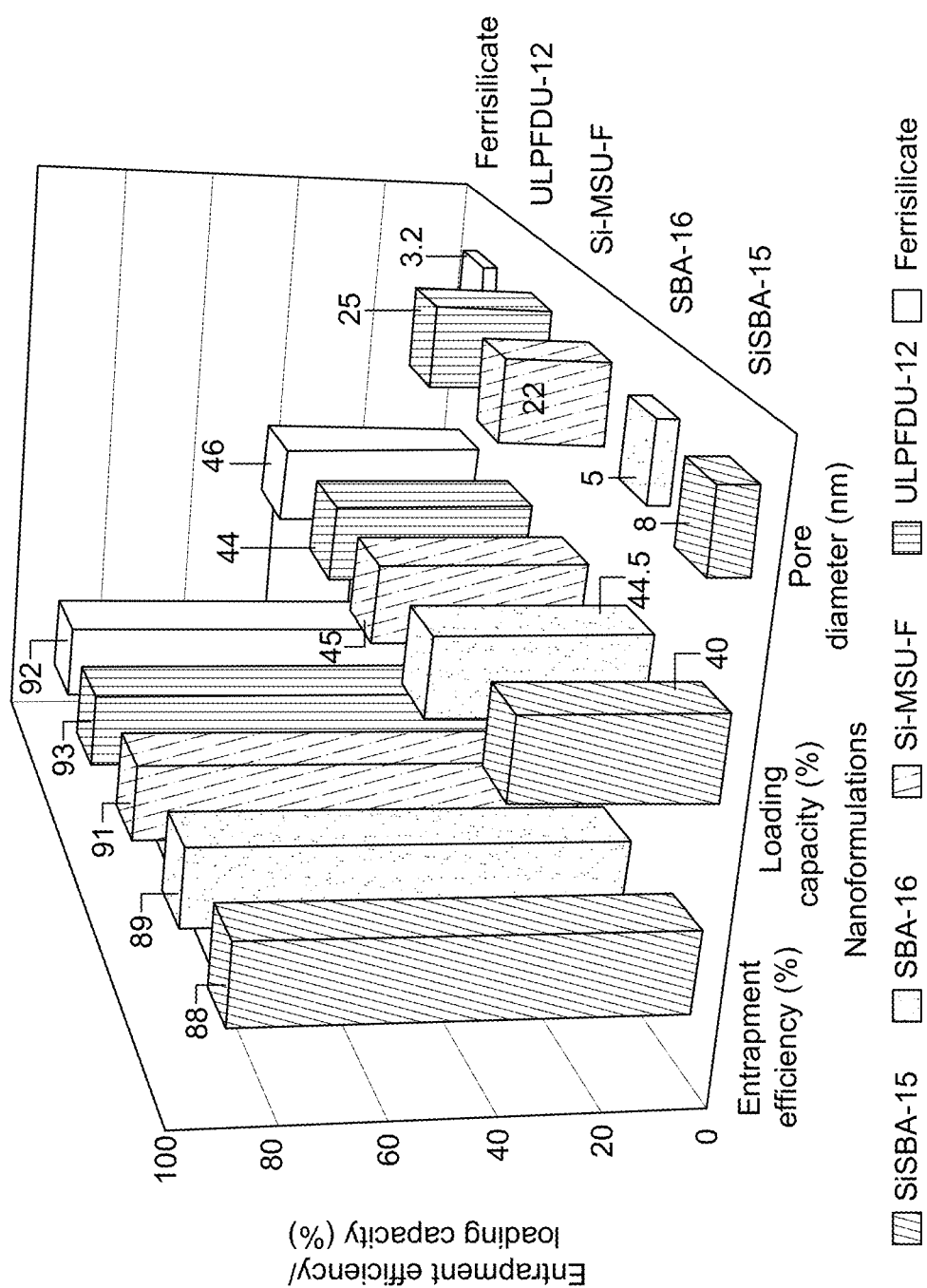
FIG. 7 is a graph depicting insulin adsorption of various silica and ferrisilicates, according to certain embodiments of the present disclosure.
Figure 8:
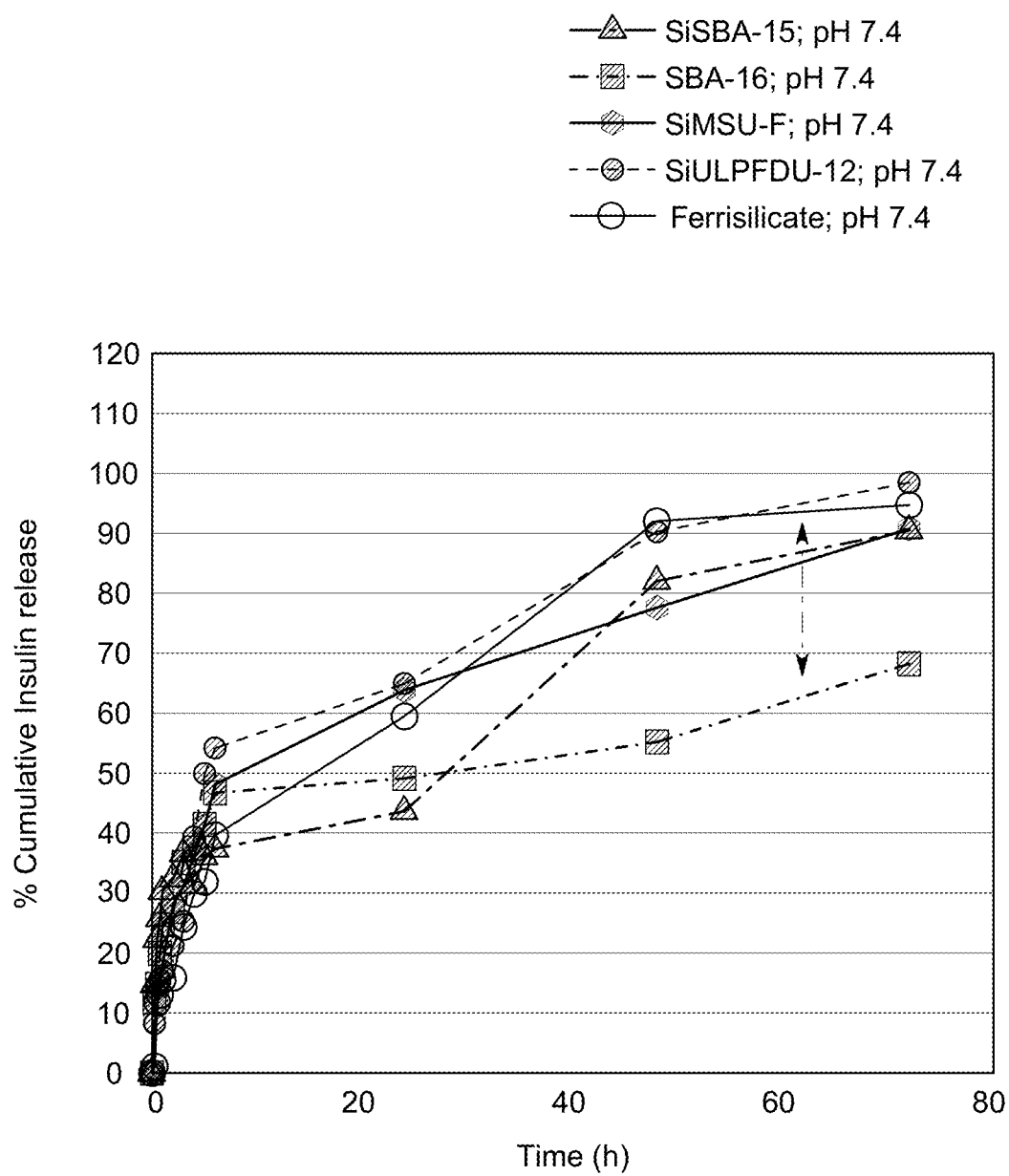
FIG. 8 is a graph depicting insulin release of various silica and ferrisilicates, according to certain embodiments of the present disclosure.

FIGS. 7-8 show insulin adsorption and release studies of various silicate and ferrisilicate materials without PEG wrapping. The various silicate materials included SiSBA-15, SBA-16, Si-MSU-F and ULPFDU-12 with different pore diameters and pore shapes. FIG. 7 shows that the ferrisilicate absorbed insulin better than the silicate materials. Furthermore, ferrisilicate showed high entrapment and loading capacity compared to the silicate materials. As shown in FIG. 8, ferrisilicate released a higher percentage of insulin over time compared to the silicate materials.

Figure 9A:
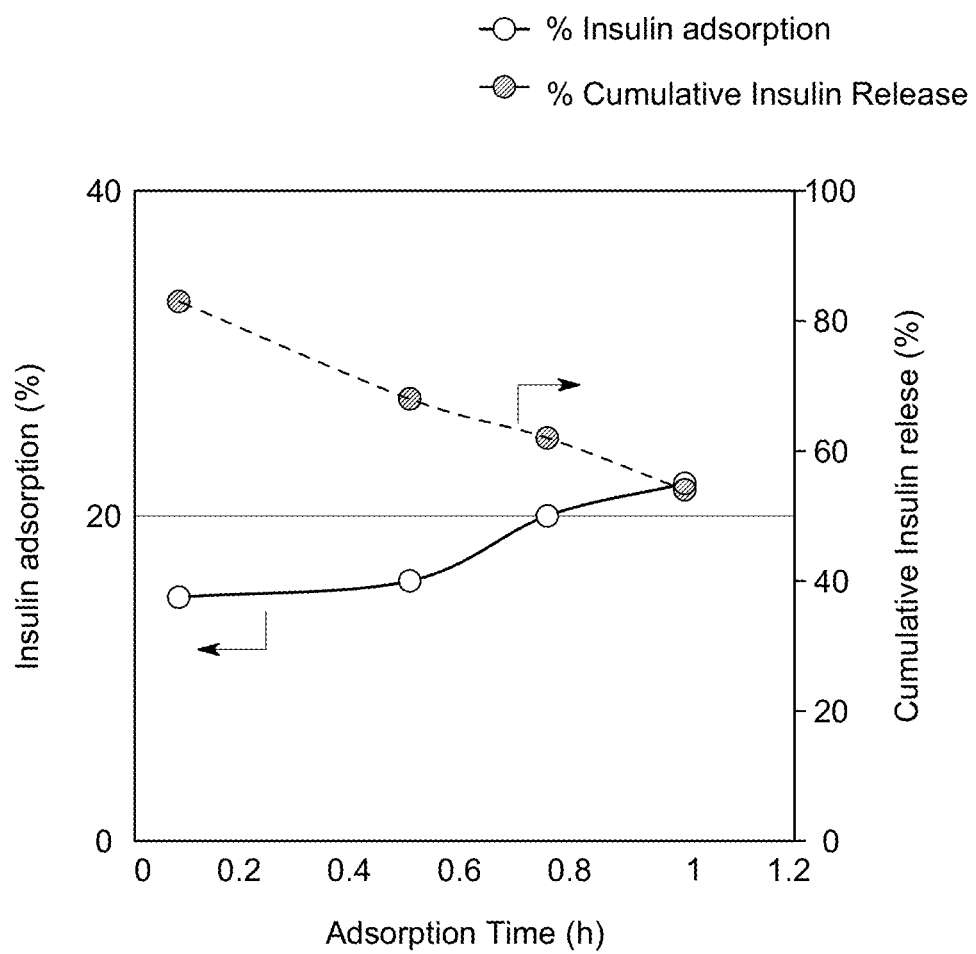
FIG. 9A is a graph depicting insulin adsorption and insulin release of ferrisilicate vs adsorption time, according to certain embodiments of the present disclosure.
Figure 9B:
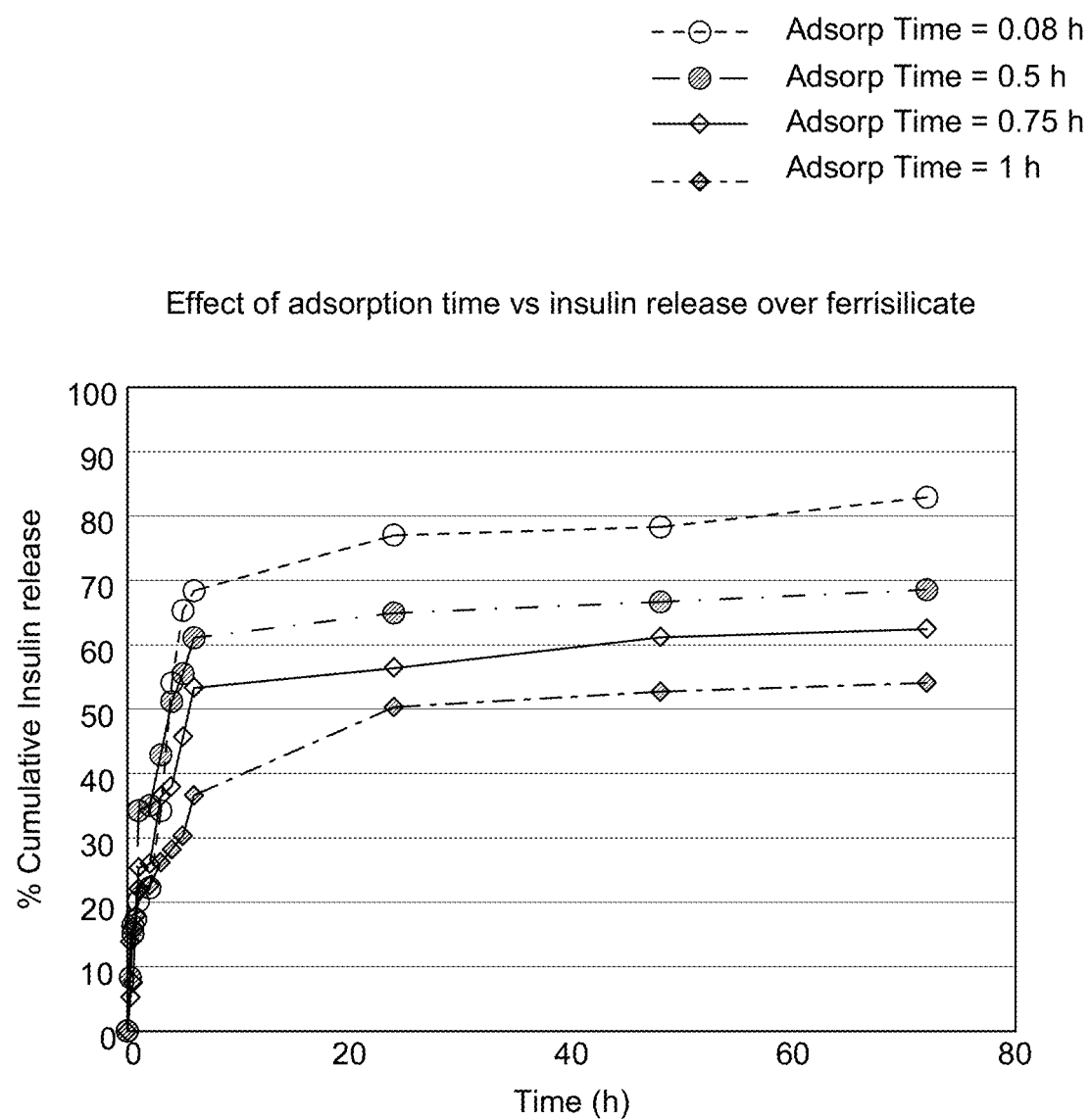
FIG. 9B is a graph depicting the effect of adsorption time vs insulin release of ferrisilicate, according to certain embodiments of the present disclosure.

FIG. 9A shows the effect of insulin adsorption time on the amount of insulin adsorbed. FIG. 9B shows the effect of adsorption time vs insulin release of Ferrisilicate/Insulin. The ferrisilicate showed an increase in the insulin adsorption with time such as 15.7%, 18.6%, 20.5%, 22% in 0.08, 0.5, 0.75, 1 hour, respectively. The higher the adsorption time made the insulin release become slower in a sustainable manner, which indicated effective entrapment with higher adsorption time.

Figure 10:
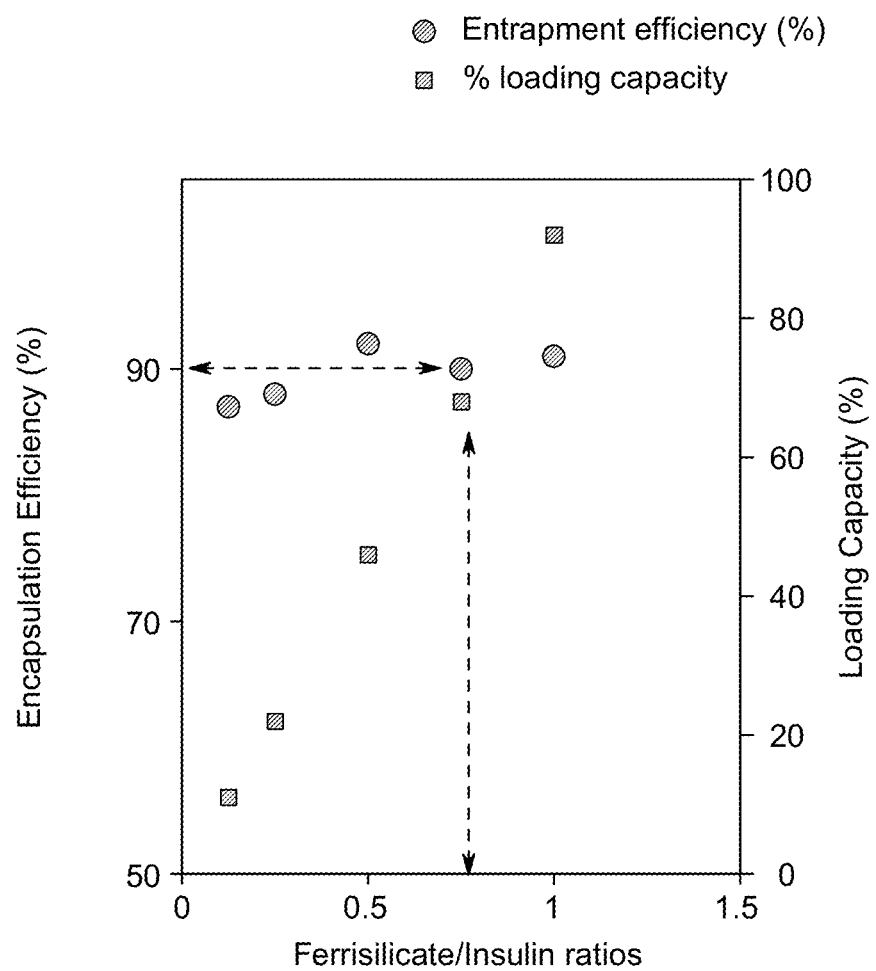
FIG. 10 is a graph depicting the effect of a mass ratio by analyzing an entrapment efficiency and a loading capacity, according to certain embodiments of the present disclosure.

FIG. 10 shows an effect of a mass ratio by analyzing an entrapment efficiency and a loading capacity. The concentration of insulin (10-80 mg) to ferrisilicate (80 mg) was varied as 0.125, 0.25, 0.5, 0.75 and 1.0. An increase in the mass ratio from 0.125 to 1.0, showed a slight increase in the entrapment efficiency from 87% to 91%. The insulin loading capacity increased significantly from 11% to 92%. The insulin to ferrisilicate mass ratio was determined to be 0.75.

Example 10: Toxicity Study

The effect of different concentrations (25-800 µg/mL) of ferrisilicate, insulin, Ferrisilicate/Insulin/PEG, Fe/KIT-6/Insulin/PEG, and Fe/KIT-6/Insulin, on the cell viability of HFF-1 cells was measured (FIGS. 11-13). The ferrisilicate, the Fe/KIT-6/Insulin, and the insulin were used as control groups to assess the cytotoxicity of empty vectors or silicate without the PEG. The Ferrisilicate/Insulin/PEG and Fe/KIT-6/Insulin/PEG showed no cytotoxicity at 25, 50, 100, 200 µg/mL after each timepoint even after 72 hours (as shown in FIG. 13) and started to show cytotoxic effect by less than 50% cell viability at the highest concentration 800 µg/mL. As shown in FIGS. 11-13 the ferrisilicate and Fe/KIT-6/Insulin were not toxic even at the highest concentration 800 µg/mL post 72 hours of treatment. The insulin had stimulated cell growth to reach to 130% in comparison to DMEM-treated cells which had a 100% cell viability and were used as control values in the present experiment.

Example 11: Diabetic Management Properties of the Materials

Figure 14:
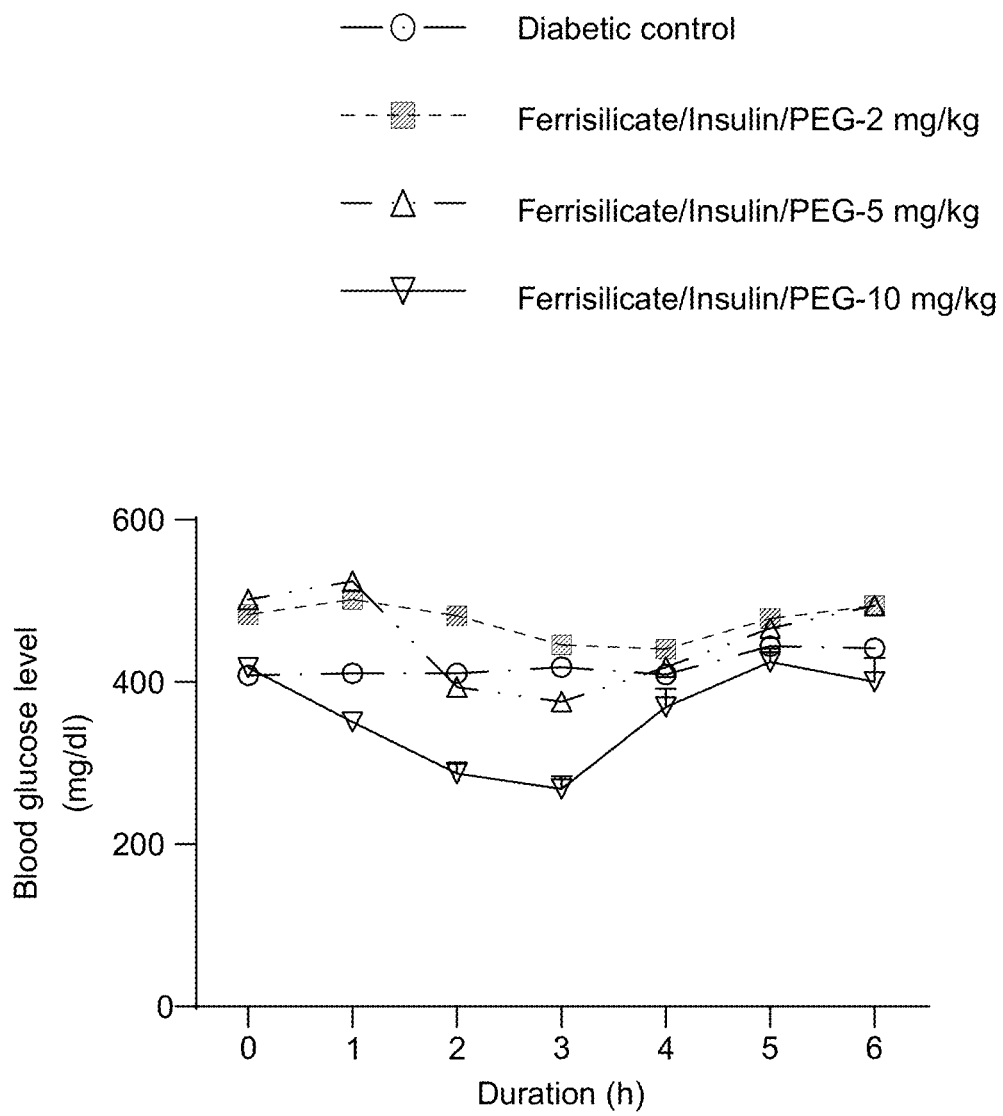
FIG. 14 is a graph depicting the effect of Ferrisilicate/Insulin/PEG at different concentrations on blood glucose levels, according to certain embodiments of the present disclosure.

FIG. 14 is a graph depicting the hypoglycemic effect of Ferrisilicate/Insulin/PEG, administered to diabetic animals at three gradient doses 2,5, and 10 milligram per kilogram (mg/kg) body weight. The blood glucose level was measured at different intervals up to 6 hours. The results of the study indicated that the hypoglycemic effect of the Ferrisilicate/Insulin/PEG at a dose of 5 and 10 mg/kg was found to be effective after 2 hours of administration. At a dose of 5 mg/kg the Ferrisilicate/Insulin/PEG reduced the blood glucose level significantly ($p=<0.0001$) until 3 hours and then started to move towards the initial blood glucose values. At 5 mg/kg, Ferrisilicate/Insulin/Peg decreased the blood glucose level from 501 to 375 milligrams per deciliter (mg/dl) (reduction of 25%). The Ferrisilicate/Insulin/PEG at 10 mg/kg body weight showed significant reduction ($p=<0.0001$) of blood glucose level after 1 hour of administration and was found to be significant until 3 hours after administration. The Ferrisilicate/Insulin/PEG reduced the blood glucose level from 417 to 268 mg/dl (35% reduction). Such effects of the Ferrisilicate/Insulin/PEG at a dose of 5 and 10 mg/kg body weight were found to be significant ($p=<0.0001$) as compared to the diabetic control. No significant effect of the Ferrisilicate/Insulin/PEG was found at 2 mg/kg body weight.

Figure 15:
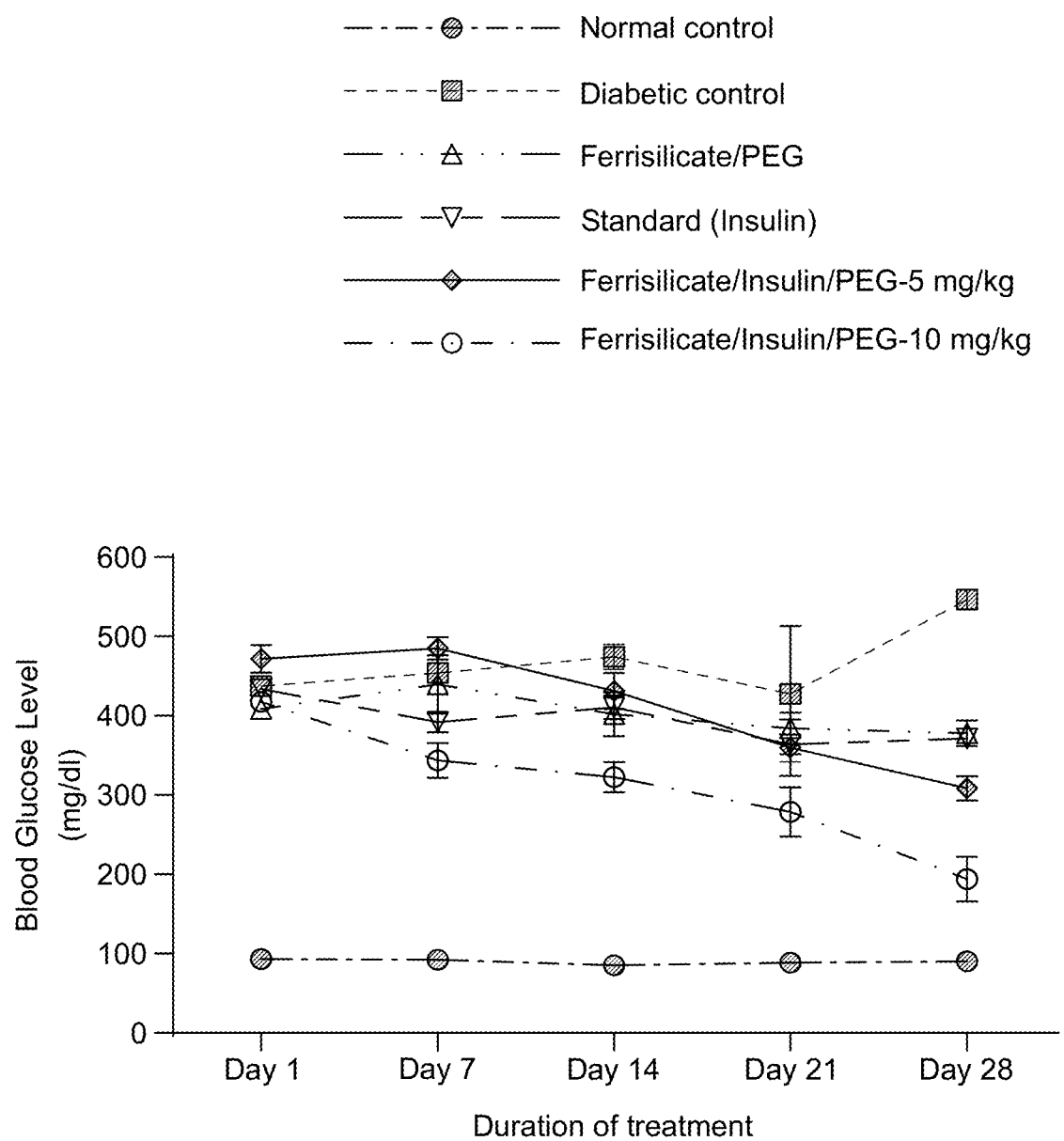
FIG. 15 is a graph depicting the effect of various formulations on fasting blood glucose levels over 28 days, according to certain embodiments of the present disclosure.

Based on the results of single dose hypoglycemic effect of the Ferrisilicate/Insulin/PEG two doses (5 and 10 mg/kg body weight) were selected to evaluate the long-term effect of the Ferrisilicate/Insulin/PEG on blood glucose levels in diabetic conditions as shown in FIG. 15. The prepared Ferrisilicate/Insulin/PEG was administered for 28 days, and blood glucose level was measured on every $7^{th}$ day. Data of the study indicates that the Ferrisilicate/Insulin/PEG at doses 5 and 10 mg/kg bodyweight had significantly ($p=<0.0001$) reduced the blood glucose on $28^{th}$ day, as compared to the initial blood glucose values at day 1. Ferrisilicate/Insulin/PEG reduced the blood glucose levels of 501 to 308 mg/dl and 417 to 194 mg/dl at doses 5 and 10 mg/kg body weight respectively. Such reductions of the blood glucose level were found to be significant as compared to diabetic control, Ferrisilicate/PEG and against a standard insulin treated group. Standard insulin significantly ($p=<0.001$) reduced the blood glucose level from 433 to 371 mg/dl. No significant effect was found in the animals of the diabetic control group and Ferrisilicate/PEG treated group.

Figure 16:
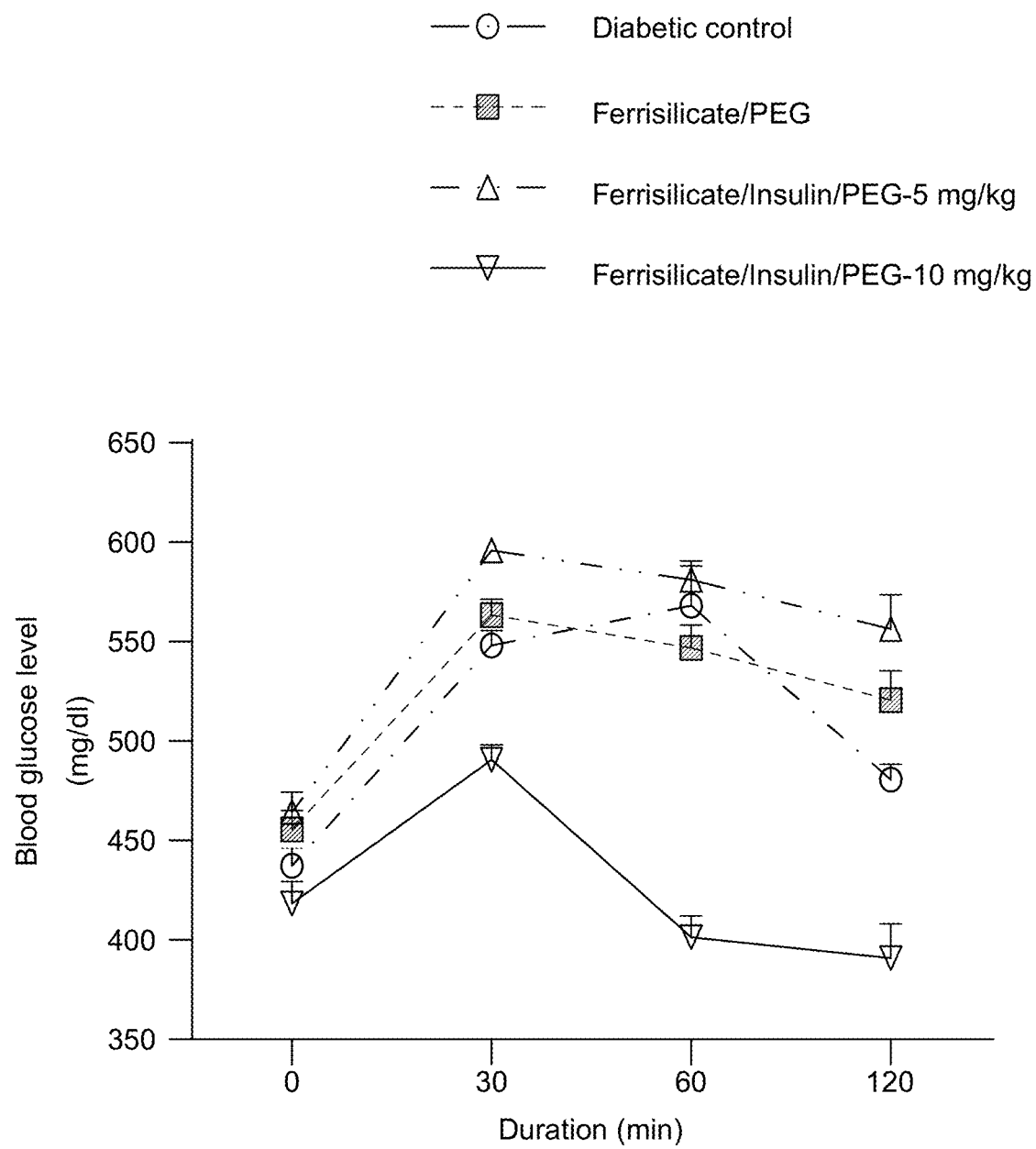
FIG. 16 is a graph depicting the effect of various formulations following oral delivery, on blood glucose levels, according to certain embodiments of the present disclosure.

The results of the oral glucose tolerance test (as shown in FIG. 16) indicated that the insulin formulation at a dose of 10 m/kg body weight had better glucose tolerance than compared to diabetic control, ferrisilicate/PEG treated and insulin formulation at 5 mg/kg body weight. The area under the curve of insulin formulation at 10 mg/kg body weight was found to be smaller compared to other groups.

Figure 17:
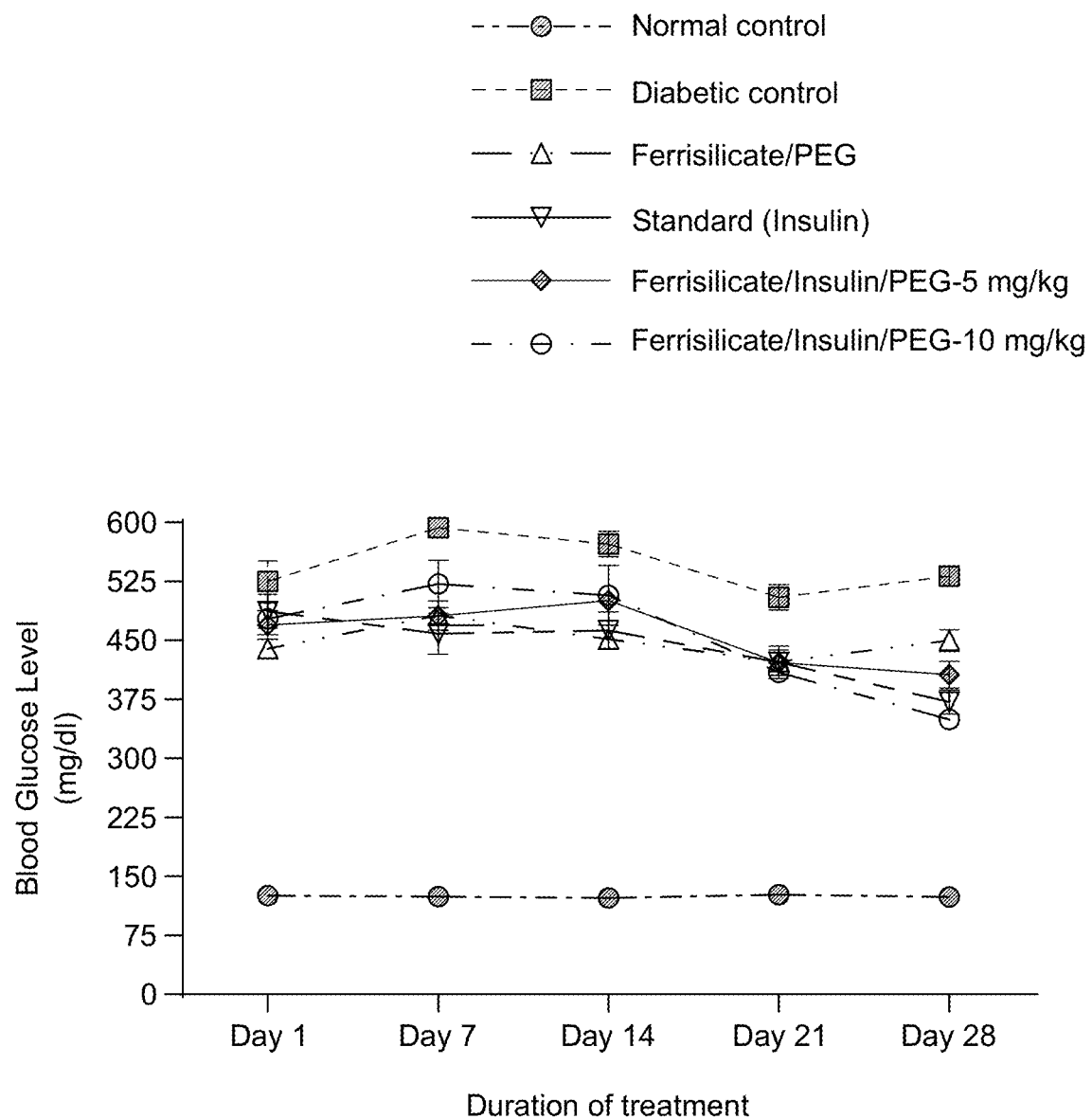
FIG. 17 is a graph depicting the effect of various formulations on non-fasting blood glucose levels over 28 days, according to certain embodiments of the present disclosure.

Non fasting blood glucose levels were measured for all the groups during the 28 days. The results of the study (FIG. 17) showed the significant ($p=<0.001$) reduction of the blood glucose levels in the groups treated with Ferrisilicate/Insulin/PEG 5 and 10 mg/kg and standard insulin. Ferrisilicate/Insulin/PEG 5 reduced the blood glucose level from 500 mg/dl at day 14 to 406 mg/dl at day 28. Ferrisilicate/Insulin/PEG 10 reduced the blood glucose level 521 mg/dl at day 7 to 349 mg/dl at day 28. Whereas standard insulin reduced the blood glucose level of 487 mg/dl at day 1 to 371 mg/dl at day 28. No significant reduction of blood glucose level was found in the diabetic control and Ferrisilicate/PEG treated group of animals.

Figure 18:
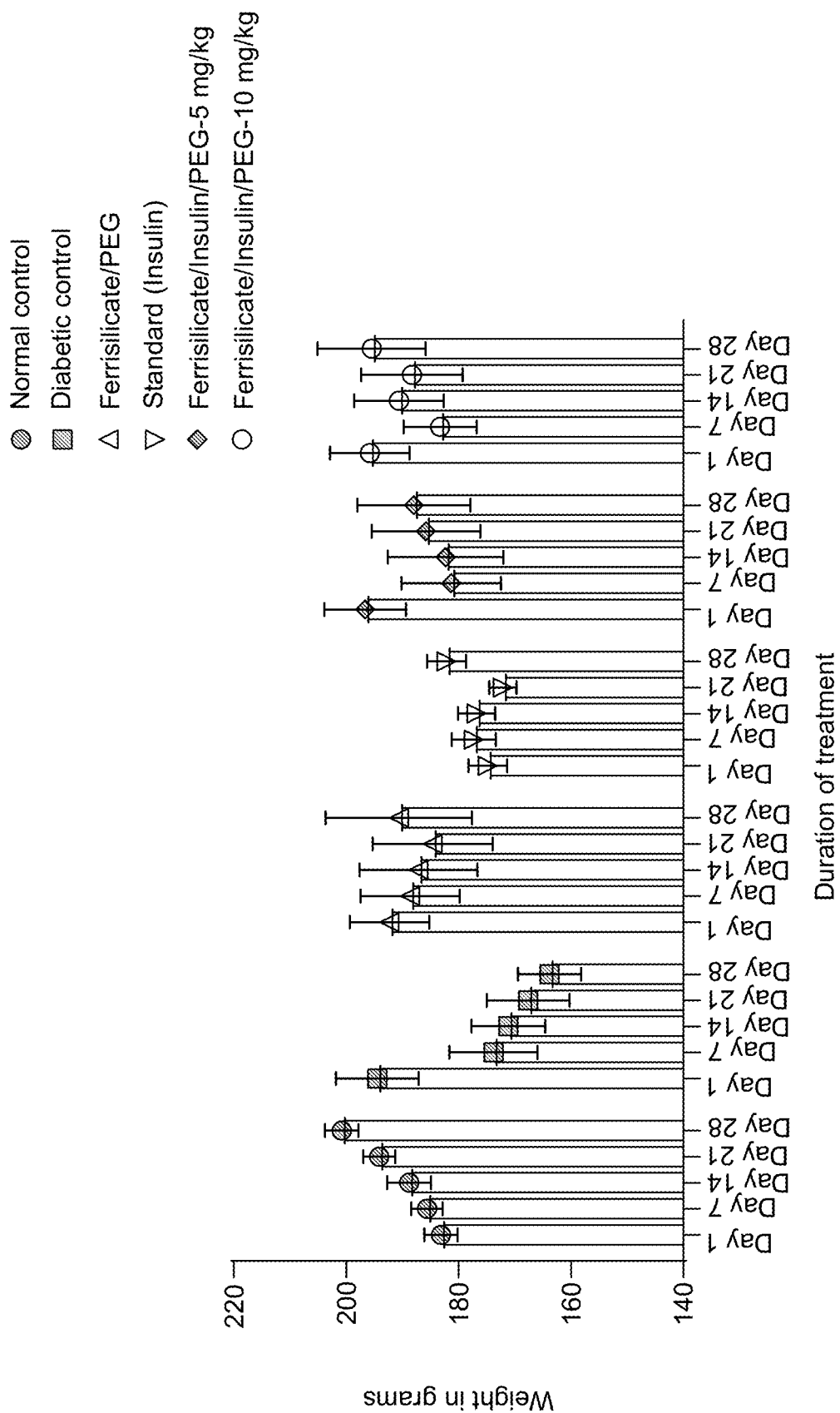
FIG. 18 is a graph depicting the effect of various formulations on body weight levels after 28 days, according to certain embodiments of the present disclosure.

Body weights were measured at each week to evaluate the effect of insulin formulation on weight of the animals during the 28 days. The changes in the body weight of animals treated with Ferrisilicate/Insulin/PEG 5 and 10 mg/kg were statistically non-significant as shown in FIG. 18. But the result of the study indicated the marked improvement in the body weight of the animals treated with Ferrisilicate/Insulin/PEG 5 and 10 as compared to the weight at day 7, whereas significant ($p=<0.001$) improvement of body weight at day 28 was found in animals treated with standard insulin treated group, as compared to the weight at day 21. A similar effect was observed in the group of animals treated with Ferrisilicate/PEG. Such improvements in the body weight of the animals treated with Ferrisilicate/Insulin/PEG and standard were found to be significant (p=<0.0001) as compared to the weight of diabetic control group. Weight of the normal group of animals increased significantly (p=<0.0001) at day 28 as compared to day 1.

Example 12: In-Vivo Study of Ferrisilicate/Insulin/PEG

The anti-diabetic potential of Ferrisilicate/Insulin/PEG was evaluated in an in-vivo study in rats. The efficacy of two insulin doses (5 and 10 mg/kg of body weight) of Ferrisilicate/Insulin/PEG was studied. After treatment, the organs (liver and pancreas) of the rats were collected for histopathological evaluation. The effect of Ferrisilicate/Insulin/PEG was compared with a control (no treatment, healthy rat), a diabetic control, ferrisilicate alone, and a standard insulin dose.

To collect the tissue at the end of the treatment time, animals were sacrificed under anesthetic conditions. These tissues were washed with phosphate-buffered saline (PBS) and fixed in 10% formalin (Tissue processing station—Tissue Teck VIP 5). The collected samples were properly stored under normal room temperature and were cut/sliced using a semiautomated microtome (Accu-Cut SRM system) into a few small pieces of 3-5 mm from each sample tissue and were separately embedded in paraffin blocks. These sliced tissues were mounted on the glass slides and were properly fixed on the glass slide with a hot plate. After this xylene was used to remove the paraffin from the tissues and was rehydrated by using a series of graded ethanol dilutions, 100%, 90%, and 70%. The rehydrated tissue sections were stained with hematoxylin and eosin (H&E) and were examined using light microscopy to determine the architecture and proportions of islet and acinar cells in the pancreas and hepatocytes in the liver.

Pancreatic acinar cells are highly specialized structures developed for synthesis, storage, and secretion of digestive enzymes. The islets of Langerhans are a cluster of cells within the pancreas that are responsible for the production and release of hormones that regulate glucose levels, and may be found dispersed in acinar lobules or in association with ducts. Histologically, four cell types make up the islets of Langerhans: the a or A cells that secrete glucagon; the R or B cells that secrete insulin; S or D cells that secrete somatostatin; and the PP cells that secrete pancreatic polypeptide. Fibrosis in the pancreas is caused by such processes as necrosis/apoptosis, inflammation or duct obstruction, of these cells and therefore variations in the amount and structure of islet and acinar cells are indicative of fibrosis.

FIGS. 19A-F depict images of the pancreatic tissue from the A) control, B) diabetic control, and subjects treated with C) ferrisilicate, D) standard insulin, E) Ferrisilicate/Insulin/PEG 5 mg/kg, and F) Ferrisilicate/Insulin/PEG 10 mg/kg. In the control group, acinar and islet cells are seen in the pancreas in normal proportions. The acinar cells are arranged in lobules and are stained darkly with prominent nuclei. The islet cells are embedded within the acinar cells and surrounded by a fine capsule (FIG. 19A). In the diabetic control, there is a severe reduction of islet cells which can be seen as small clusters with irregular margins embedded in predominant acinar cells. Focal fibrosis is seen with a disarrangement of pancreatic acinar cells (FIG. 19B). When treated with ferrisilicate alone, the pancreatic architecture appears normal with a normal proportion of acinar and islet cells, however the islet cell cluster margins appear ill defined (FIG. 19C). When treated with standard insulin, the pancreatic histology is similar to that of the diabetic control (FIG. 19D). When treated with 5 mg/kg of Ferrisilicate/Insulin/PEG, the pancreatic tissue has a normal proportion of acinar cells and islet cells, however, the islet cell cluster margins are not well defined and focal fibrosis is seen with focal disruption of the pancreatic architecture (FIG. 19E). When treated with 10 mg/kg of Ferrisilicate/Insulin/PEG, the pancreatic tissue has a normal proportion of acinar cells and islet cells, with some of the islet cell cluster margins being well defined, and focal fibrosis is seen with a normal pancreatic architecture (FIG. 19F). Compared to the diabetic control, treatment with Ferrisilicate/Insulin/PEG results in a normal proportion of acinar cells and islet cells. Although not wishing to be bound to any particular theory, the Ferrisilicate/Insulin/PEG is thought to protect islet cells and reduce the severe reduction of islet cells in diabetic patients.

FIGS. 20A-F depict images of the pancreatic tissue from the A) control, B) diabetic control, and subjects treated with C) ferrisilicate, D) standard insulin, E) Ferrisilicate/Insulin/PEG 5 mg/kg, and F) Ferrisilicate/Insulin/PEG 10 mg/kg. The control group shows a normal architecture of hepatic lobules which have plates or cords of hepatocytes radiating from a central vein and forming a network. These cords of hepatocytes are separated by narrow intervening sinusoids lined by endothelial cells and Kupffer cells. No inflammatory cells are seen (FIG. 20A). In the diabetic control, the liver shows focal crowding of hepatocytes around the central vein with loss of normal architecture, and the focal hepatocytes show tiny vacuoles suggestive of degenerative changes (FIG. 20B). When treated with ferrisilicate alone, the liver histology shows a normal hepatic architecture with a dilated central vein and occasional degenerating hepatocytes (FIG. 20C). When treated with standard insulin, the liver histology shows mostly a normal lobular architecture with normal cords of hepatocytes with intervening patent sinusoids with focal congestion with only occasional hepatocytes showing degenerative changes and no inflammation is seen (FIG. 20D). When treated with 5 mg/kg of Ferrisilicate/Insulin/PEG, the liver histology shows a congested central vein, sinusoids with focal vacuolar degeneration of hepatocytes, and focal inflammatory infiltrate around the central vein (FIG. 20E). When treated with 10 mg/kg of Ferrisilicate/Insulin/PEG, the liver histology shows a normal liver architecture with no features of degeneration and only congested central veins are seen (FIG. 20F). Overall, compared to the diabetic control, treatment with Ferrisilicate/Insulin/PEG shows recovery to a normal liver architecture.

The present disclosure provides a biocompatible and pH sensitive, Ferrisilicate/Insulin/PEG composition designed for insulin release. The pore filling effect of the insulin inside the cubic shaped pores facilitated extended insulin release. Wrapping with the PEG led to maintained insulin release without affecting the pores. The Ferrisilicate/Insulin/PEG exhibited a low cytotoxicity to HFF-1 cells and diabetic management in an in vivo study. The Ferrisilicate/Insulin/PEG composition exhibited potential in managing diabetes.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A method of delivering insulin, comprising:
orally administering to a subject a composition comprising,
a ferrisilicate material having one or more pores, the one or more pores having an average pore size of from 2 nm to 5 nm;
polyethylene glycol; and
insulin;
wherein the insulin at least partially penetrates the pores of the ferrisilicate material to form a ferrisilicate insulin composite,
wherein the polyethylene glycol, at least partially enfolds the ferrisilicate insulin composite, and
wherein the composition has a cumulative insulin release of about 40% after 500 hours following oral administration.

2. The method of claim 1, wherein the ferrisilicate material has an atomic ratio of silicon to iron of 10-300 to 1.

3. The method of claim 1, wherein the ferrisilicate material has cubic shaped pores.

4. The method of claim 1, wherein the insulin is amorphous.

5. The method of claim 1, wherein the ferrisilicate insulin composite has a surface area of 300-350 square meter per gram (m2/g).

6. The method of claim 1, wherein the composition has a pore volume of 0.1-0.5 cubic centimeter per gram (cm3/g).

7. The method of claim 1, wherein at least a portion of the polyethylene glycol is hydrogen-bonded to the insulin.

8. The method of claim 1, wherein the ferrisilicate insulin composite has 5-90 weight percent (wt %) insulin based on the total weight of the ferrisilicate insulin composite.

9. The method of claim 1, wherein the ferrisilicate insulin composite has 60-80 wt % insulin based on the total weight of the ferrisilicate insulin composite.

10. The method of claim 1, wherein 1-100 milligrams (mg) of the composition per kg body weight of the subject is orally administered.

11. The method of claim 1, wherein the blood glucose level of the subject is decreased following oral administration of the composition.

12. The method of claim 11, wherein the blood glucose level is decreased by 5-40% after 1-3 hours following oral administration of the composition.

13. The method of claim 1, wherein the composition is administered daily.

14. The method of claim 13, wherein the blood glucose level of the subject is decreased by 20-50% after 28 days.

15. The method of claim 11, wherein the blood glucose level is decreased by a greater amount than a same method administering only the insulin.

16. The method of claim 1, wherein the ferrosilicate material is substantially free of iron oxide as measured by X-ray diffraction (XRD).

17. The method of claim 1, wherein the ferrisilicate has an average pore size of 3.2 nm.

* * * * *